(12) United States Patent
O'Keeffe et al.

(10) Patent No.: US 9,149,515 B2
(45) Date of Patent: Oct. 6, 2015

(54) INTERFERON-ALPHA-PRODUCING BONE MARROW DENDRITIC CELLS

(75) Inventors: Meredith O'Keeffe, Melbourne (AU); Hubertus Hochrein, Munich (DE)

(73) Assignee: BAVARIAN NORDIC A/S, Kvistgaard ( * ) Notice: Subject to any disclaimer, the term of this patent is extended or adjusted under 35 U.S.C. 154(b) by 35 days.

(21) Appl. No.: 13/701,435

(22) PCT Filed: Jun. 3, 2011

(86) PCT No.: PCT/EP2011/002747
§ 371 (c)(1),
(2), (4) Date: Nov. 30, 2012

(87) PCT Pub. No.: WO2011/151078
PCT Pub. Date: Dec. 8, 2011

(65) Prior Publication Data
US 2013/0122044 A1    May 16, 2013

Related U.S. Application Data

(60) Provisional application No. 61/350,571, filed on Jun. 2, 2010.

(30) Foreign Application Priority Data

Dec. 22, 2010    (EP) .................................. 10015987

(51) Int. Cl.
| | |
|---|---|
| *C12N 5/071* | (2010.01) |
| *C12N 5/00* | (2006.01) |
| *C12N 5/02* | (2006.01) |
| *A61K 39/00* | (2006.01) |
| *C12N 5/0784* | (2010.01) |

(52) U.S. Cl.
CPC .............. *A61K 39/00* (2013.01); *C12N 5/0639* (2013.01); *A61K 2039/5154* (2013.01); *A61K 2039/5158* (2013.01)

(58) Field of Classification Search
None
See application file for complete search history.

(56) References Cited

U.S. PATENT DOCUMENTS

2008/0267994 A1    10/2008    Hochrein et al.

OTHER PUBLICATIONS

Megyeri et al., 1995, Mol. Cell. Biol. vol. 15: 2207-2218.*
Ni et al., 2002, J. Biol. CHem. vol. 277: 12689-12696.*
Seillet et al., 2012, Blood, vol. 119: 454-464.*
Di Domizio et al., Blood, vol. 114: 1794-1802.*
Hochrein et al., 2004, PNAS, vol. 101 11416-11421.*
European Patent Office Communication enclosing the Extended European Search Report for EP Application No. 10015987, dated May 13, 2011.
International Search Report for PCT/EP2011/002747, dated Jul. 8, 2011.
Written Opinion of the International Searching Authority for PCT/EP2011/002747, dated Jul. 8, 2011.
D.M. Ashley et al., "Bone Marrow-generated Dendritic Cells pulsed with Tumor Extracts or Tumor RNA Induce Antitumor Immunity . . . ," J. Exp. Med. 186(7):1177-1182 (1997).
D. Bimczok et al., "Site-specific expression of CD11b and SIRPalpha (CD172a) on dendritic cells: implications . . . " Eur. J. Immunol. 35:1418-1427 (2005).
A. Jamin et al., "Characterization of conventional & plasmacytoid dendritic cells in swine secondary lymphoid organs & blood," Vet. Immunol. Immunopathol. 114:224-237 (2006).
Y.-J. Liu, "IPC: Professional Type 1 Interferon-Producing Cells and Plasmacytoid Dendritic Cell Precursors," Annu. Rev. Immunol. 23:275-306 (2005).
A. Summerfield et al., "The porcine dendritic cell family," Dev. Comp. Immunol. 33:299-309 (2009).
Spies et al., Vaccination with Plasmid DNA Activates Dendritic Cells via Toll-Like Receptor 9 (TLR9) but Functions in TLR9-Deficient Mice. J Immunol 2003; 171:5908-5912.

* cited by examiner

*Primary Examiner* — Amy Juedes
(74) *Attorney, Agent, or Firm* — The Law Firm of Salvatore Arrigo and Scott Lee LLP

(57) ABSTRACT

A novel dendritic cell type has been identified within bone marrow, termed myelos interferon dendritic cells (miDC). These novel cells possess the high IFN-alpha producing activity of pDC, but they also display a wide TLR responsiveness along with T-cell stimulation capacities that more closely resemble the conventional DC populations. Moreover, these cells appear less prone to apoptosis upon activation stimuli, including viruses. These cells constitute a novel bone marrow innate immune cell type, ideally geared to linking innate and adaptive immune responses via their potent IFN-alpha production and high cell stimulatory capacity.

18 Claims, 19 Drawing Sheets

A

CD40

CD86

CD8α

B

CD45R

C

2216

LPS

R837

PIC

P3Cys

Media

RAG-GFP

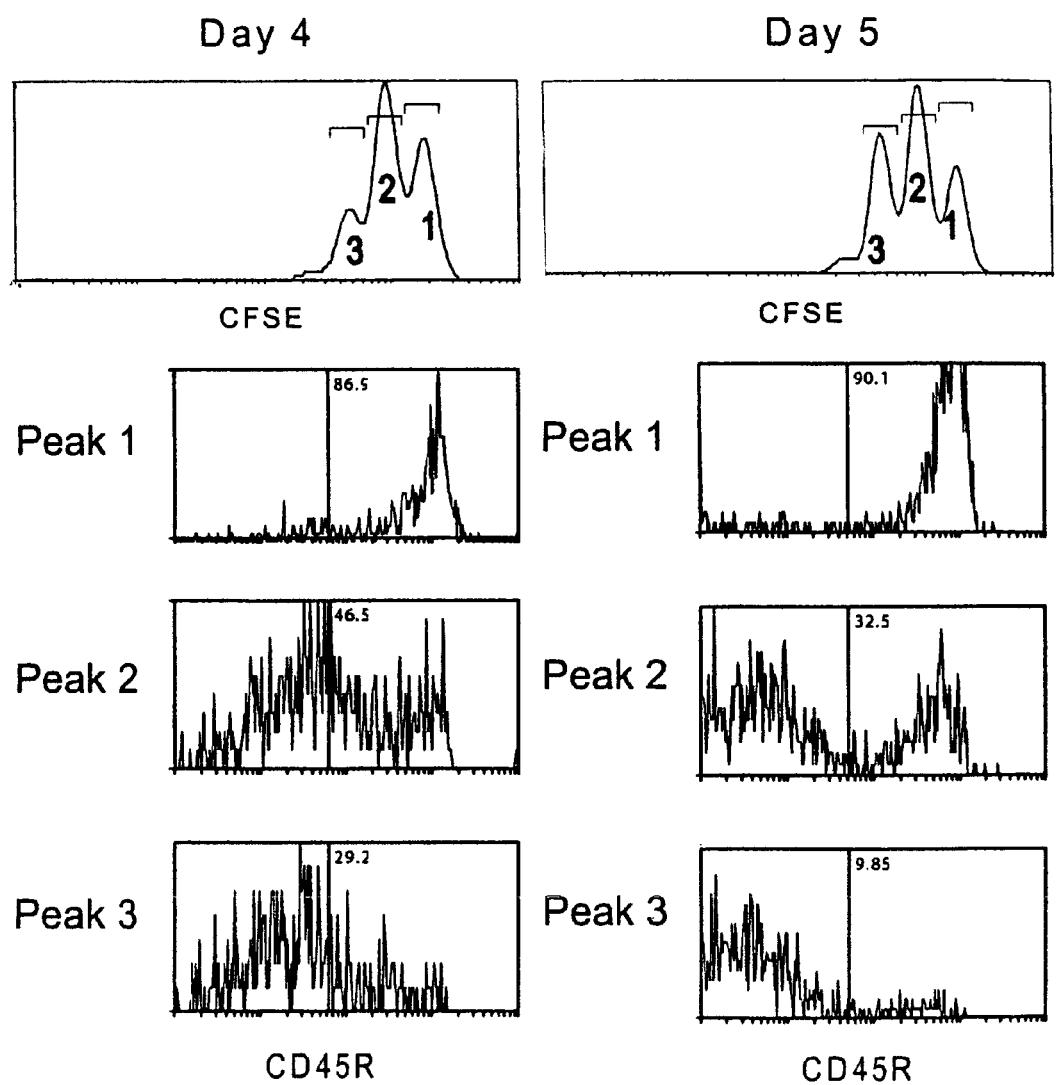

INTERFERON-ALPHA-PRODUCING BONE MARROW DENDRITIC CELLS

This application is a National Phase application under 35 U.S.C. §371 of International Application No. PCT/EP2011/002747, filed Jun. 3, 2011, and claims the benefit under 35 U.S.C. §365 of European Application No. 10015987, filed Dec. 22, 2010, and the benefit under 35 U.S.C. §119(e) of U.S. Provisional Application No. 61/350,571, filed Jun. 2, 2010, the disclosures of which are incorporated herein by reference in their entirety.

FIELD OF THE INVENTION

The present invention relates to the field of immunotherapy, in particular to the field of the production of interferons (IF) by dendritic cells. The invention relates to a novel specific dendritic cell type responsible for the production of IFN-alpha (IFN-α) and in vitro and in vivo uses thereof. The present invention relates to therapeutic applications based on the novel IFN-α producing dendritic cell type. The present invention also relates to the use of double stranded (ds) nucleic acids capable of inducing an anti-infectious response, in particular an anti-viral response in a subject by inducing the production of IFN-α in the novel specific dendritic cell type. The invention further relates to methods for producing IFN-α and/or generating or obtaining the novel IFN-α producing dendritic cells. The present invention also relates to methods for detecting and/or screening for the novel IFN-α producing dendritic cells. In addition, the invention relates to ex vivo methods for inducing the production of IFN-α in the novel dendritic cells and uses thereof.

BACKGROUND OF THE INVENTION

Dendritic cells (DCs) are heterogeneous cells that act as the sentinels of the immune system. They recognise pathogens and their products via the expression of numerous cell surface, endosomal and cytoplasmic pattern recognition receptors (PRR) that are differentially expressed amongst different DC subsets (Diebold 2009; Hochrein and O'Keeffe 2008; Luber et al. 2010). The differential expression of PRR lends different DC subsets with the ability to recognise pathogens via distinct and overlapping mechanisms.

DCs can be divided into two major categories: conventional DCs (cDC) and plasmacytoid DCs (pDCs). The term "classic" or "conventional" DCs (cDCs) has recently been used to oppose lymphoid organ-resident DCs to pDCs. Non-lymphoid organ DCs, on the other hand are mainly called tissue DCs. While non-lymphoid tissue DCs are also different from pDCs, and primary non-lymphoid tissue DCs can be found in lymph nodes on migration but are not cDCs, the tem cDCs refers to all non-pDCs whether they are present in lymphoid or non-lymphoid tissues.

Mouse cDC can be recognized by the expression of high levels of CD11c and MHCII (Hochrein and O'Keeffe 2008). Mouse pDC have a characteristic high production of type I Interferon and have the phenotype $CD11c^{int}MHCII^{lo}CD11b^{-}CD205^{-}$.

Mouse and human pDC share many surface molecules, such as CD45RA, CD45RB, and CD68. They also express a similar pattern of intracellular Toll-like receptors. Expression of CD11b is able to differentiate two different subsets of cDC in human.

There is a close relationship between human and mouse DC (O'Keeffe et al., 2003). Mouse blood cells with the phenotype $CD11c^{lo}CD11b^{-}CD45RA^{hi}$ closely resemble human pDC by morphology and function. In human blood, $CD11c^{-}IL3R^{+}CD45RA^{+}$ pDC can be found, which can produce a large amount of interferon upon stimulation.

The cDC can be further divided into several subsets based upon tissue location and surface phenotype. In mice, the surface markers CD4 and $CD8^{+}$ are useful markers to distinguish functionally different DC subsets. The unifying function of all cDC is the ability to induce naive T cells into the cell cycle. The exceptional ability of cDC to process and present antigen in the context of MHCI and MHCII endows them with the title 'professional antigen presenting cells'. The $CD8\alpha^{+}$ cDC have the additional feature of 'cross-presentation', the ability to present exogenous antigen in the context of MHCI (Villadangos and Schnorrer 2007). The functions of cDC also extend to cytokine and chemokine production. High IL-12p70 production is a hallmark of CD8α+ cDC and high levels of chemokines including RANTES, MIP-1α and MIP-1β are produced by $CD8\alpha^{-}$ cDC (Hochrein et al. 2001; Maldonado-Lopez et al. 1999; Proietto et al. 2004). Additionally IL-6, IL-8, IL-10, IL-15, IL-18, IL-23, IL-27 and TNF-α have been reported to be expressed by cDC under different stimulatory conditions.

On the other hand the pDC, generally considered as part of the DC 'family', lack typical cDC characteristics, including surface phenotype and morphology and also normally lack the ability to stimulate naive T cells (O'Keeffe et al. 2002). If given specific PRR stimuli they can induce some T cell division, more than B cells or macrophages, but typically in the order of 10-fold or less than that of the cDC (Villadangos and Young 2008). Unlike cDC the pDC continually present antigens on MHCII molecules once they are activated and, as a result, can continue to present new viral antigens during the course of infection (Young et al. 2008). The importance of this function of pDC during an ongoing infection is not yet elucidated. Instead the pDC, also referred to as natural interferon-producing cells (NIPC), are renowned for their production of Type I interferons (IFN-I) in response to viral or bacterial stimuli and mimics thereof (Gilliet et al. 2008; Kadowaki 2009). The categorization of the pDC as a member of the DC 'family' rests upon morphological and phenotypical features that they display upon activation. Namely, the pDC upregulate co-stimulation markers and MHC molecules to levels resembling the cDC and they rapidly acquire the typical stellate morphology of cDC. Based on these features, it was initially proposed that this IFN-I producing DC subset would be the ultimate anti-viral cell, combining within the same cell the innate IFN response and potent CTL stimulation. To date, these high hopes have not been realised. The IFN-I response of pDC is remarkable, but their concomitant ability to induce CTL is in most cases relatively poor.

The past 10 years have seen an explosion in the knowledge of innate recognition of pathogens. The discovery of an increasing number of PRR, including the Toll-like receptor (TLR) family (of TLR1-13) and the nature of their ligands, have shed light on many aspects of pathogen recognition. It is clear that via differential expression of PRR, cells of the innate immune system of both mouse and humans have the ability to recognise pathogenic lipids and carbohydrates and remarkably PRR also enable the recognition of nucleic acids of both pathogenic and self origin.

The recognition of nucleic acids can be via 4 different TLR; TLR3 recognizes dsRNA, TLR7, and TLR 8 (truncated in the mouse) recognize ssRNA and TLR9 recognizes ssDNA. The TLR 7, 8, and 9-dependent recognition of nucleic acids occurs within cellular endosomes and is critically dependent upon the adaptor molecule MyD88. Non-TLR dependent nucleic acid recognition pathways also exist, but are less well defined than the TLR-mediated recognition pathways. RNA recognition that is TLR and MyD88-independent occurs via a cytoplasmic localised recognition complex involving RigI and Mda-5 molecules and can also involve the cytoplasmic Nod-like receptors. The cytoplasmic recognition of DNA, at least B-DNA (right-handed B-form DNA), is independent of the RigI and Mda-5 molecules, but shares with the Rig pathway downstream signalling molecules including TBK-1 and IKKi and can include molecules such as DAI and 3' repair exonuclease 1 (Trex1). An inflammasome complex mediated by binding of AIM2 to dsDNA can also be involved in sensing of cytoplasmic dsDNA, leading to caspase-1 dependent cleavage of IL-1β.

The pDC of both mouse and humans recognise DNA via TLR9. As a consequence of endoplasmic reticulum to lysosome internal trafficking of TLR9 and differential expression of molecules that are involved in the TLR9 signalling complex, such as high constitutive expression of IRF7, the pDC, unlike any other cell previously described, have the ability to produce extremely high levels of IFN-I upon TLR9 ligation. Synthetic CpG-containing oligonucleotides (ODN) are sufficient for triggering of IFN-I from pDC and, in fact, the pDC are the only cell type known to produce IFN-I to CpG-ODN. This statement holds true in mouse in most lymphoid organs. However, as previously shown, when bone marrow (BM) cells are depleted of pDC, there remains IFN-α production in response to CpG-ODN (Hochrein et al. 2004). These data suggested that cells other than CD45R$^+$CD45RA$^+$ pDC were capable of TLR9-mediated IFN-α production. This finding contradicts the current dogma that pDC are the only cell type that produce IFN-I in response to TLR9 mediated ligation. The biological relevance of this observation extends beyond responses to CpG-ODN; many viruses have now been shown to activate cells via TLR9-mediated recognition (Hochrein and O'Keeffe 2008) and leaves the possibility that another cell type in BM could respond rapidly to TLR9 ligation with high levels of IFN-α production.

The BM is the birthplace of hematopoiesis and the source of life-long stem cells. It is also a haven for plasma cells and memory T cells and the cells involved in bone morphogenesis. However, it is also a site frequently infected by viruses, and yet the knowledge of the cellular responses to viruses or other pathogens in the bone marrow is extremely limited. With the advent of BM transplantation and a desire to understand the cellular entities potentially involved in transplantation rejection, it is of upmost importance to clarify the cell types within BM.

It has been reported that human early pre-pDC, that do not share the pDC phenotype, also have the ability to produce high levels of Type I IFN (Chen et al. 2004). These interferon producing cells (IPCs) exhibited a plasmacytoid morphology. The IPCs were also CD11c$^-$ and strongly expressed TLR9. The paper also reports the isolation of immature DC that were CD11c$^+$ and preferentially expressed TLR3. IPC, but not CD11c$^+$ immature DC, could produce high levels of IFN-α upon stimulation with Herpes simplex virus. The CD11c$^+$ immature DC described in Chen et al. 2004 did not express TLR9 and produced little IFN-α in response to Herpes Simplex virus. Thus these cells cannot respond rapidly to TLR9 ligation with high levels of IFN-α production.

When spleen, thymus, mesenteric or subcutaneous lymph nodes are depleted of pDC using pDC-specific antibodies and magnetic beads, the IFN-α activity in response to CpG-ODN is abolished. However, when bone marrow (BM) cells are depleted of pDC there remains IFN-α production in response to CpG-ODN (Hochrein et al 2004).

Based on the above, there is a need in the art for the isolation of cell types other than pDC that can respond rapidly to TLR9 ligation with high levels of IFN-α production.

SUMMARY OF THE INVENTION

The inventors of the present application identified a non-pDC cell type within BM that produces IFN-α in response to nucleic acids of both pathogenic and self origin. These cells have been named myelos interferon DC (miDC), and display the phenotype of an immature cDC when isolated ex vivo. With an analog of a ligand recognized by a pathogen-associated pattern recognition receptor (PRR), they produce enormous amounts of IFN-α that are equivalent on a per cell basis to the IFN-α produced by pDC. Unlike pDC, the miDC are activated by GM-CSF and LPS and acquire the phenotype of mature cDC. Upon virus infection, like the pDC, the miDC produce IFN-α, but unlike the pDC, they survive extremely well before and after infection. With activation, the miDC strongly stimulate naive T cells in an allogeneic mixed lymphocyte reaction. Moreover, miDC are potent presenters of viral-encoded protein to naive T cells. In all, the inventors of the present application are the first to provide a non-pDC cell type that possesses pathogen-associated PRR-dependent IFN-α production as well as potent T cell stimulatory capacity. Accordingly, the present invention provides the following items:

[1] A method for preparing an immunotherapeutic agent, comprising the steps of: (a) providing bone marrow-derived non-plasmacytoid dendritic cells (non-pDCs) that are CD11b$^{-/lo}$ and CD172$^+$ (Sirpα); and (b) modifying ex vivo the non-pDCs of step (a) such that they are loaded with one or more antigens.

[2] The method of item [1], wherein the step of modifying ex vivo the non-pDCs is selected from the group consisting of: (i) incubating the one or more antigens and the dendritic cells in culture, (ii) immune complex-mediated uptake of the one or more antigens by the dendritic cells, (iii) electroporation of the cells in the presence of the one or more antigens, (iv) viral transduction of the one or more antigens, and (v) lipofection or transfection of mRNA or DNA encoding the one or more antigens.

[3] The method of item [1] or [2], wherein the antigen is a viral antigen, a bacterial antigen, a fungal antigen, a parasite antigen or a tumor antigen.

[4] A pharmaceutical composition comprising the immunotherapeutic agent obtained by the method of any one of items [1] to [3], optionally further comprising a pharmaceutically acceptable carrier or diluent.

[5] A vaccine comprising the immunotherapeutic agent obtained by the method of any one of items [1] to [3], optionally further comprising a pharmaceutically acceptable adjuvant.

[6] A preparation comprising the immunotherapeutic agent obtained by the method of any one of items [1] to [3] for use in eliciting an antigen-specific immune response in a subject.

[7] The preparation of item [6], wherein the patient is suffering from an infectious disease or cancer.

[8] The preparation of item [7], wherein the infectious disease is a viral infection, a bacterial infection, a parasitic infection or a fungal infection.

[9] The preparation of any one of items [6] to [8], wherein the antigen-specific immune response is antigen-specific T cell stimulation, preferably antigen-specific stimulation of naive T cells.

[10] A ligand recognized by a pattern recognition receptor inducing the production of IFN-α in non-plasmacytoid dendritic cells (non-pDCs) that are CD11b$^{-/lo}$ and CD172$^+$ (Sirpα) for use in treating a subject suffering from an infectious disease of the bone marrow or bone marrow cancer, wherein the IFN-α inducing ligand is to be administered to the bone marrow of said subject.

[11] The ligand of item [10], wherein the infectious disease is a viral infection, a bacterial infection, a parasitic infection or a fungal infection of the bone marrow, preferably a viral infection of the bone marrow.

[12] A method for inducing the production of IFN-α in a population of non-plasmacytoid dendritic cells (non-pDCs) that are CD11b$^{-/lo}$ and CD172$^+$ (Sirpα) comprising contacting ex vivo bone marrow-derived non-pDCs that are CD11b$^{-/lo}$ and CD172$^+$ (Sirpα) with a ligand recognized by a pattern recognition receptor inducing the production of IFN-α in said non-pDCs.

[13] An in vitro method for isolating, detecting or screening for IFN-α producing non-plasmacytoid dendritic cells (non-pDCs), comprising the steps of: (a) providing a population of bone marrow-derived non-pDCs that are CD11b$^{-/lo}$ and CD172$^+$ (Sirpα); and (b) detecting the production of IFN-α after stimulating or inducing the production of IFN-α in the cell population of step (a) with a ligand recognized by a pattern recognition receptor inducing the production of IFN-α in said non-pDCs.

[14] An IFN-α producing bone marrow-derived non-plasmacytoid dendritic cell (non-pDC) that is CD11b$^{-/lo}$ and CD172$^+$ (Sirpα).

[15] The cell of item [14] for use in treating a subject suffering from an infectious disease or cancer.

The cell of item [15], wherein the infectious disease is a viral infection, a bacterial infection, a parasitic infection or a fungal infection, preferably a viral infection.

[17] The cell of item [15] or [16], wherein said cell is contacted ex vivo with a ligand recognized by a pattern recognition receptor inducing the production of IFN-α in said cell prior to administration to the subject.

[18] The ligand of item [10] or [11], or the method of item [12] or [13], or the cell of item [17], wherein the pattern recognition receptor is a pathogen-associated pattern recognition receptor.

[19] The ligand of item [18], or any of the methods of item [18], or the cell of item [18], wherein the pathogen-associated pattern recognition receptor is a cell surface, endosomal and/or cytoplasmic pathogen-associated pattern recognition receptor.

[20] The ligand of item [19], or any of the methods of item [19], or the cell of item [19], wherein the ligand is a TLR3 ligand, a TLR7 ligand, a TLR8 ligand, or a TLR9 ligand.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and other references mentioned herein are incorporated by reference in their entirety. In case of conflict, the present specification, including definitions, will control. The materials, methods, and examples are illustrative only and not intended to be limiting. Other features and advantages of the invention will be apparent from the drawings, detailed description, and from the claims.

DETAILED DESCRIPTION OF THE INVENTION

A non-pDC cell type has been identified within bone marrow (BM) that produces IFN-α in response to nucleic acids of both pathogenic and self origin. These cells are referred to as myelos (bone marrow in Greek language) interferon dendritic cells (miDC). The novel cell type "miDC" identified by the inventors of the present application displays the phenotype of an immature cDC when isolated ex vivo. With an appropriate stimulus, i.e. a ligand of pathogenic origin that is recognized by a pathogen-associated PRR (such as a nucleic acid of pathogenic origin), miDC produce enormous amounts of Type I IFN that are equivalent on a per cell basis to the IFN-α produced by pDC. miDC can be discriminated by their phenotypic characteristics from pDC and other cDC.

The BM is well established as a primary lymphoid organ, but it also provides niches for B cells and naive T cells that in situ respond to blood-borne antigens. The BM is thus established as an important and unique secondary lymphoid organ. It is also a preferential site for memory T cell homing and homeostatic proliferation and for long-lived plasma cells. Given these factors, it is important to understand the cell types that may interact with lymphocytes in situ in the BM.

A novel DC type has been identified in BM. It has been found that, apart from the pDC, there is another DC in BM that produces high amounts of IFN-α, namely the miDC identified by the inventors of the present application. Like the pDC, the miDC have a potent ability to produce IFN-α in response to nucleic acids of both pathogenic and self origin and, upon activation, acquire the expression of CD8 and CD45R. However, this is where the similarity between the two cell types ends.

The miDC provided by the present invention clearly respond differently to a ligand of pathogenic origin that is recognized by a pathogen-associated PRR than the pDC. They are strongly matured at the cell surface and produce extremely high levels of IL-6 to such a stimulus and yet pDC hardly produce detectable IL-6 to a corresponding stimulus. Like the pDC, the miDC respond to TLR7 ligand (such as R837), but they also produce low levels of IFN-α to such a stimulus. The miDC, but not pDC, also respond to TLR2 and TLR4 ligands with cell surface activation and low IL-6 production. They also mature in response to GM-CSF in vitro, a factor that has no effect on the surface phenotype of pDC.

In sharp contrast to the pDC, the survival of miDC in all conditions tested was high, at least 60% after two days. In contrast to pDCs, miDCs that died could not be rescued by Bcl2 expression. This also contrasted with the phenotype of pDC. The high survival was not due to detectable proliferation of the cells. The miDC appear to have a capacity to undergo one to two divisions, but this was only observed when they were 'spiked' into FLDC cultures.

A striking feature of the miDC is their ability to present virally encoded antigen and to induce proliferation of specific T cells to this antigen. Given the high survival of virally-infected miDC, they are a potential long-lived source of viral antigen and an inducer of CTL in the bone marrow.

Several viruses are known to be found in BM. The best example of a 'BM-trophic' virus in mouse is LCMV (Lymphocytic Choriomeningitis Virus). Acute LCMV infections in mice lead to BM failure during the first week of infection as a direct result of Type I IFN mediated ablation of hematopoietic precursor cells. HSV-1 and dengue virus infection of BM cells have been implicated in hematopoietic defects. In addition, hematopoietic abnormalities in HIV patients are attributable, at least in part, to the replication of HIV in hematopoietic cells in the BM.

Cytomegalovirus (CMV) is a Herpes virus that specifically targets hematopoietic precursor cells in the BM and is of particular concern in immunosuppressed individuals. In mouse pox infections, ECTV (Ectromelia virus) is found in BM of both resistant and susceptible mouse strains. Replicating poxviruses, including avipox virus ALVAC and vaccinia, used as vectors in human vaccine trials, infect as yet uncharacterized CD33+ cells within BM.

The significance of miDC within the BM, cells that produce large amounts of IFN-I and have the ability to strongly stimulate naive T cells, relates to both the primary and secondary lymphoid organ roles of this organ. IFN-I produced by miDC and pDC in response to viruses potentially impacts upon hematopoiesis since it is established that high levels of IFN-I can ablate hematopoietic precursors leading to acquired anemia or skewing of precursor development. IFN-I acts as an adjuvant and activates and enhances DC, CTL, and B cell responses and thus potentially enhances innate and adaptive immune responses to BM encountered antigen. In the case of miDC, the production of IFN-I, as well as their ability to stimulate T cells, suggests their direct involvement in T cell activation. This also raises the possibility that miDC may be deleterious in BM transplant situations, having the ability to strongly stimulate graft or host-derived T cells. Their response to TLR9 and TLR7 stimulation also marks them, along with pDC, as potential contributors to SLE pathology. The high IL-6 production of miDC also suggests that they may play a role in survival of BM plasma cells (Kawano et al. 1995).

The miDC provided by the present invention are a novel cell type with potential to aid viral clearance from the BM, but also with attributes that could be deleterious in transplant situations or in autoimmune conditions such as SLE. Unlike pDC, the miDC are activated by GM-CSF and LPS and acquire the phenotype of mature cDC. Upon virus infection, like the pDC, the miDC produce IFN-α, but unlike the pDC, they survive extremely well before and after infection. With activation, the miDC strongly stimulate naive T cells in an allogeneic mixed lymphocyte reaction. Moreover, the miDC are potent presenters of viral-encoded protein to naive T cells. Thus, the miDC possesses TLR9-dependent IFN-α production and potent T cell stimulatory capacity. The miDCs of the present invention have an extremely high survival rate after stimulation with TLR ligands and also against viruses, which contrasts greatly with the pDC and also other DC subtypes. The miDC is the first example of a cell that makes high levels of the anti-viral cytokine IFN-α, and at the same time can strongly stimulate T cells to proliferate.

The present invention provides a bone marrow (BM)-derived non-plasmacytoid dendritic cell (non-pDC) that is $CD11b^{-/lo}$. This is the minimum characterization of the novel cell type named "miDC" identified by the inventors of the present application. In the present invention, the term "miDC" encompasses not only the cell type that is characterized as a BM-derived non-pDC that is $CD11b^{-/lo}$, but encompasses any further characterization of the novel cell type as described herein. For example, the novel cell type is preferably $CD11b^{-/lo}$ and CD172+ (Sirpα). Thus, in various embodiments the term "miDC" as used herein encompasses a BM-derived non-pDC that is $CD11b^{-/lo}$ and CD172+ (Sirpα). Accordingly, the term "miDC" encompasses every definition of the novel cell type as described herein and, thus, encompasses various embodiments of the novel cell type in accordance with the definitions of the novel cell type given herein.

As used herein, the term "novel cell type" relates to the miDC identified by the inventors of the present application. Furthermore, as used herein, the term "novel cell type" basically includes the definition that the novel cell type is a BM-derived non-pDC. Thus, the miDC identified by the inventors of the present application basically is a BM-derived non-pDC. Furthermore, the novel cell type is basically $CD11b^{-/lo}$.

As described above, the novel cell type is preferably $CD11b^{-/lo}$ and CD172+ (Sirpα). Accordingly, in accordance with the understanding that the novel cell type provided by the present invention basically is a BM-derived non-pDC, the novel cell type that is preferably $CD11b^{-/lo}$ and CD172+ (Sirpα) is a novel BM-derived non-pDC that is preferably $CD11b^{-/lo}$ and CD172+ (Sirpα). More preferably, the novel cell type is $CD11b^{-/lo}$, CD172+ (Sirpα) and CD45RA−. Still more preferably, the novel cell type is $CD11b^{-/lo}$, CD172+ (Sirpα), CD45RA− and CD11c+. Even more preferably, novel cell type is $CD11b^{-/lo}$, CD172+ (Sirpα), CD45RA−, CD11c+ and $CD24^{int}$.

In further preferred embodiments the novel cell type is $CD11b^{-/lo}$ and CD45RA−. Preferably, the novel cell type is $CD11b^{-/lo}$, CD45RA−, and CD11c+. More preferably, the novel cell type is $CD11b^{-/lo}$, CD45RA−, CD11c+ and $CD24^{int}$.

In further preferred embodiments the novel cell type is $CD11b^{-/lo}$ and CD11c+. More preferably, the novel cell type is $CD11b^{-/lo}$, CD11c+, and $CD24^{int}$.

In further preferred embodiments the novel cell type is $CD11b^{-/lo}$ and $CD24^{int}$. More preferably, the novel cell type is $CD11b^{-/lo}$, $CD24^{int}$ and CD172+ (Sirpα). Still more preferably, the novel cell type is $CD11b^{-/lo}$, $CD24^{int}$, CD172+ (Sirpα) and CD45RA−.

In further preferred embodiments the novel cell type is $CD11b^{-/lo}$, CD172+ (Sirpα), and CD11c+. More preferably, the novel cell type is $CD11b^{-/lo}$, CD172+ (Sirpα), CD11c+ and $CD24^{int}$.

In further preferred embodiments the novel cell type is $CD11b^{-/lo}$, CD45RA−, and $CD24^{int}$.

Thus, the miDC provided by the present invention may be characterized by at least one of the following cell surface markers: CD11b, CD172 (Sirpα), CD45RA, CD11c and CD24. These cell surface markers may provide for a structural definition of the miDC provided by the present invention and may thus provide for distinguishing from conventional dendritic cells described in the art. Of course, as one of ordinary skill in the art will understand the miDCs of the present invention are not limited to the said surface markers. The terms "cell surface marker(s)" and "surface marker(s)" are used herein interchangeably.

Accordingly, the miDC provided by the present invention may be further characterized by at least one the following further surface markers: CD3, CD19, CD20, CD49b, NK1.1, Ly6G, BDCA-1, BDCA-2, BDCA-3, BDCA-4, CD4, and CD8α. The miDC provided by the present invention show further surface markers which can be identified by the person skilled in the art and which are also encompassed by the present invention.

The present invention provides an isolated cell population of miDCs in accordance with the present invention. Accordingly, the present invention basically provides an isolated cell population of BM-derived non-pDCs that are $CD11b^{-/lo}$. The isolated cell population provided by the present invention can comprise any of the miDCs described herein, i.e. including miDCs with any or all of the surface markers of miDC described herein. Preferably, the isolated cell population comprises at least 10% of miDCs in accordance with the present invention. More preferably, the isolated cell population comprises at least one of 10%, 20%, 30%, 40%, 50%, 55%, 60%, 65%, 70%, 75%, 80%, 85%, 90%, or 95% of miDCs in accordance with the present invention. Most preferably, the isolated cell population comprises 100% of miDCs in accordance with the present invention.

In various embodiments, the isolated cell population provided by the present invention comprises at least $10^4$ miDCs according to the present invention. Preferably, the isolated cell population comprises at least $10^5$ miDCs according to the present invention. More preferably, the isolated cell population comprises at least $10^6$ miDCs according to the present invention. Still more preferably, the isolated cell population comprises at least $10^7$ miDCs according to the present invention. Even more preferably, the isolated cell population comprises at least $10^8$ miDCs according to the present invention. In still further preferred embodiments, the isolated cell population comprises at least $10^9$ miDCs according to the present invention.

In various embodiments, the isolated cell population comprises at least one of 10%, 20%, 30%, 40%, 50%, 55%, 60%, 65%, 70%, 75%, 80%, 85%, 90%, or 95% of miDCs of the present invention and/or at least one of $10^4$, $10^5$, $10^6$, $10^7$, $10^8$ or $10^9$ miDCs of the present invention.

The present invention provides methods for the isolation of miDCs according to the present invention, wherein the method comprises selecting a cell population of miDCs in accordance with the present invention and culturing the selected dendritic cells. In various embodiments, the step of selecting a cell population of miDCs in accordance with the present invention comprises selecting a cell population of miDCs that have the capacity to produce high levels of IFN-α in response to an appropriate stimulus. The nature of such an appropriate stimulus is described herein elsewhere. The miDC may be isolated from any mammal, including mice, rats, primates, and humans.

In various embodiments, precursor cells may be incubated with an agent enhancing miDC formation in vitro and in vivo. In a preferred embodiment, the agent enhancing miDC formation may be Flt3-ligand (FL) or a M-CSF receptor ligand. The addition of FL may also increase the number of miDCs. The administration of FL to increase miDCs may be combined with stimulation of the miDCs with a nucleic acid or analog thereof according to the present invention to increase the production of IFN-α.

Furthermore, in accordance with the present invention, precursor cells can be incubated with a cytokine. Preferably, the cytokine is selected from the group consisting of IL-3, GM-CSF, IL-4, and IFN-γ.

The present invention provides miDCs which can be mouse or rat miDCs. The present invention also provides miDCs which are human miDCs.

In various embodiments, the method for the isolation of miDCs according to the present invention comprises removing miDCs from the cell population with antibodies directed against surface markers described herein, i.e. surface markers of the miDC of the present invention described herein as well as further surface markers of the miDC which can be identified by the skilled person by techniques established in the art.

In various embodiments, the method for the isolation of miDCs according to the present invention comprises collecting bone marrow cells and depleting the collected bone marrow cells of pDCs. Preferably, the collected bone marrow cells are depleted of pDCs using anti-CD45RA antibodies. Here, the use of anti-CD45RA antibodies follows techniques known in the art. More preferably, the anti-CD45RA antibodies are coupled to magnetic beads to facilitate depletion of the collected bone marrow cells from pDCs. The coupling of the antibodies to magnetic beads may be directly or indirectly.

In various embodiments, the method for the isolation of miDCs according to the present invention comprises purifying light density cells from a collected or selected cell population described herein. For example, a collected or selected cell population may be subjected to a gradient to separate high density T cells, B cells, and macrophages from light density cells. Accordingly, in various embodiments the present invention provides a method for the isolation of light density miDCs. In various embodiments, a collected or selected cell population may be subjected to a gradient to separate high density T cells, B cells, and macrophages from light density cells, followed by isolating or separating miDCs from the light density cells. In various embodiments, bone marrow cells provided or collected in accordance with the present invention may be bound to antibodies against CD45RA and/or CD11c and then be sorted in order to achieve this isolation. Of course, other methods known in the art may also be used in order to achieve this isolation. Such other methods are also encompassed by the present invention.

In various embodiments, the method for the isolation of miDCs according to the present invention comprises incubating the cells or population of cells with at least one of a TLR7 ligand, a TLR8 ligand and a TLR9 ligand, and detecting the production of IFN-α. Thus, in various embodiments the method for the isolation of miDCs according to the present invention comprises after stimulating or inducing the production of IFN-α in a cell population comprising miDC according to the present invention with at least one of a TLR7 ligand, a TLR8 ligand, and a TLR9 ligand.

In various embodiments, miDCs of the present invention may be isolated, for example, by cell sorting, using antibodies to at least one of the surface markers described herein. Preferably, the surface marker is selected from the group consisting of CD3, CD19, CD49b, NK1.1, and Ly6G.

In various embodiments isolated cell populations according to the present invention can be enriched for miDCs of the present invention using miDC surface markers as described herein. Here, the use of surface markers for enriching miDCs of the present invention follows standard techniques known in the art.

In various embodiments, miDCs of the present invention are isolated by removing those cells that express high levels of CD11b. In various embodiments, an isolated miDC cell population can be enriched for cells that are CD45RA$^-$, CD11c$^+$, CD3$^-$, CD19$^-$, CD49b$^-$, NK1.1$^-$, and/or Ly6G$^-$. Preferably, the isolated cell population is enriched for cells that are CD11b$^{-/lo}$, CD45RA$^-$ and CD11c$^+$. More preferably, the isolated cell population is enriched for cells that are CD11b$^{-/lo}$, CD45RA$^-$, CD11c$^+$, and CD3$^-$. Still more preferably, the isolated miDC cell population is enriched for cells that are CD11b$^{-/lo}$, CD45RA$^-$, CD11c$^+$, CD3$^-$, and CD19$^-$. Even more preferably, the isolated miDC cell population is enriched for cells that are CD11b$^{-/lo}$, CD45RA$^-$, CD11c$^+$, CD3$^-$, CD19$^-$, and CD49b$^-$. In further preferred embodiments, the isolated cell population is enriched for cells that are CD11b$^{-/lo}$, CD45RA$^-$, CD11c$^+$, CD3$^-$, CD19$^-$, CD49b$^-$, and NK1.1$^-$. In still further preferred embodiments, the isolated cell population is enriched for cells that are CD11b$^{-/lo}$, CD45RA$^-$, CD11c$^+$, CD3$^-$, CD19$^-$, CD49b$^-$, NK1.1$^-$, and Ly6G$^-$.

In various embodiments, miDCs of the present invention are isolated by removing those cells that express CD4 and/or CD8α. Preferably, the isolated cell population is enriched for cells that are CD11b$^{-/lo}$, CD45RA$^-$, CD11c$^+$, CD4$^-$ and/or CD8α$^-$. More preferably, the isolated cell population is enriched for cells that are CD11b$^{-/lo}$, CD45RA$^-$, CD11c$^+$, CD3$^-$, CD4$^-$ and/or CD8α$^-$. Still more preferably, the isolated miDC cell population is enriched for cells that are CD11b$^{-/lo}$, CD45RA$^-$, CD11c$^+$, CD3$^-$, CD19$^-$, CD4$^-$ and/or CD8α⁻. Even more preferably, the isolated miDC cell population is enriched for cells that are CD11b⁻/ˡᵒ, CD45RA⁻, CD11c⁺, CD3⁻, CD19⁻, CD49b⁻, CD4⁻ and/or CD8α⁻. In further preferred embodiments, the isolated cell population is enriched for cells that are CD11b⁻/ˡᵒ, CD45RA⁻, CD11c⁺, CD3⁻, CD19⁻, CD49b⁻, NK1.1⁻, CD4⁻ and/or CD8α⁻. In still further preferred embodiments, the isolated cell population is enriched for cells that are CD11b⁻/ˡᵒ, CD45RA⁻, CD11c⁺, CD3⁻, CD19⁻, CD49b⁻, NK1.1⁻, Ly6G⁻, CD4⁻ and/or CD8α⁻.

In various embodiments, miDCs of the present invention may be isolated using antibodies to at least one of the surface markers CD24, Flt3, CD45R, CD40, CD80, CD86, and MHCII.

In various embodiments, miDCs of the present invention may be isolated using antibodies to at least one of TLR2, TLR3, TLR4, TLR7, and TLR9.

In various embodiments, miDCs of the present invention may be isolated using antibodies to the surface markers CD24, CD11c, and/or BDCA-1. Accordingly, in various embodiments cell sorting according to the present invention may be performed in order to isolate miDCs expressing CD24, CD11c, and/or BDCA-1. Other well-known techniques can similarly be used in order to isolate miDC of the present invention expressing CD24, CD11c, and/or BDCA-1.

The miDC according to the present invention produce enormous amounts of IFN-α that are equivalent on a per cell basis to the IFN-α produced by pDC with an analog of a ligand recognized by a pathogen-associated PRR. In various embodiments, the miDCs according to the present invention have the capacity to produce high levels of IFN-α in response to an appropriate stimulus as described herein elsewhere. Such miDCs are encompassed by the present invention. Likewise, in various embodiments, a cell population comprising miDCs according to the present invention has the capacity to produce high levels of IFN-α in response to an appropriate stimulus. Such miDC cell populations are encompassed by the present invention. A high level of IFN-α production in accordance with the present invention means a level of at least 5 times higher than the level measurable with unstimulated miDC. In various embodiments, the miDC can produce "very high levels" of IFN-α upon stimulation with an appropriate stimulus, such as a CpG. In this context, a "very high levels" of IFN-α production means a level of at least 20 times higher than the level measurable with unstimulated miDC. In further embodiments, the stimulated miDC can produce a level of IFN-α that is at least one of 2 times, 3 times, 4 times, 8 times, 15 times, 20 times, 25 times, 50 times, and 100 times of the level of IFN-α production of an unstimulated miDC.

As used herein, a stimulus appropriate to induce the production of IFN-α in miDCs according to the present invention is a ligand recognized by a pathogen-associated pattern recognition receptor (PRR). While such a ligand is preferably of pathogenic origin, the present invention also encompasses non-pathogenic ligands as stimuli that are appropriate stimuli to induce the production of IFN-α in miDCs according to the present invention, as long as such non-pathogenic ligands are recognized by a pathogen-associated PRR in accordance with the present invention. Examples of non-pathogenic ligands that are recognized by a pathogen-associated PRR in accordance with the present invention are CpGs, for example CpG2216.

In various embodiments, the stimulus appropriate to induce the production of IFN-α in miDCs in accordance with the present invention is at least one of a TLR3 ligand, a TLR7 ligand, a TLR8 ligand and a TLR9 ligand. Preferably, the stimulus is of Herpes virus origin or of poxvirus origin. More preferably, the stimulus is of MVA virus origin.

In various embodiments, the stimulus appropriate to induce the production of IFN-α in miDCs in accordance with the present invention is a nucleic acid or analog thereof. The nucleic acid may be DNA or RNA, preferably ds DNA or ds RNA, including analogs thereof. Suitable dsDNA may comprise natural dsDNA such as genomic DNA which might be of prokaryotic or eukaryotic or viral origin, e.g. mitochondrial DNA, plasmid DNA, viral DNA or thymic DNA. To facilitate the uptake of the DNA, methods for enhanced uptake such as liposomes, electroporation, or nanoparticles may be employed.

In the present invention, the nucleic acid is DNA or RNA, including analogs thereof. In various embodiments of the present invention, the nucleic acid is ds nucleic acid, including analogs thereof. In various embodiments of the present invention, the nucleic acid is ss nucleic acid, including analogs thereof. In various embodiments of the present invention, the DNA is ds DNA, including analogs thereof. In various embodiments, the RNA is ds RNA, including analogs thereof. In various embodiments of the present invention, the DNA is ss DNA, including analogs thereof. In various embodiments of the present invention, the RNA is ss RNA, including analogs thereof.

In various embodiments, the ds nucleic acid or analog thereof according to the present invention is produced or provided by a virus. Preferably, the virus is a dsDNA virus, a dsRNA virus or a ssRNA virus. The dsRNA or dsDNA according to the present invention, including analogs thereof, can be produced or provided by a dsDNA virus, a dsRNA virus, an ssDNA virus, or a positive ssRNA virus. Thus, in various embodiments, the analog of a ds nucleic acid according to the present invention is a ss nucleic acid, which is processed or can be processed to a ds nucleic acid.

In various embodiments, the virus is a positive ssRNA virus, such as a Togavirus, a Flavivirus, an Astrovirus, a Picornavirus, a Calicivirus, a Hepevirus, a Nodavirus, an Arterivirus, or a Coronavirus. In various embodiments, the virus is a dsRNA virus, such as Reovirus or a Birnavirus. In various embodiments, the virus is a retrovirus, such as an HIV-1, HIV-2, or SIV. In various embodiments, the virus is a ds DNA virus, such an Asfarvirus, an Iridovirus, a Polyomavirus, a Papillomavirus, a Papovavirus, an Adenovirus, a Herpesvirus, a Poxvirus, or a Hepadnavirus. In a preferred embodiment, the virus is a poxvirus, such as an Orthopoxvirus or a Parapoxvirus. Preferably, the poxvirus is a variola virus, a cowpoxvirus, a camelpoxvirus, or a vaccinia virus. Particularly preferred is a MVA virus. In various embodiments, the virus is a Herpesvirus, such as a Herpes simplex virus (HSV 1 or HSV 2), Varicella Zoster virus, human cytomegalovirus, Epstein-Barr virus, and Kaposi sarcoma-associated Herpes virus.

In various embodiments, the nucleic acid or analog thereof that stimulates the production of IFN-α in miDCs of the present invention is DNA or RNA. Preferably, the DNA is dsDNA and the RNA is ssRNA. In various embodiments, the DNA or RNA is produced or provided by a DNA virus or a RNA virus. In preferred embodiments, the virus is a Poxvirus, Herpesvirus, Togavirus, or a Coronavirus.

In various embodiments, the miDC according to the present invention are in vitro activated miDC. This applies preferably to miDCs used in the treatment of a subject in need thereof according to the present invention. As used herein, activated miDC means miDC activated by exposing to an antigen in order to present the antigen or miDC activated to produce IFN-α by an appropriate stimulus in accordance with the present invention. Thus, an activated miDC according to the present invention may be a miDC activated by being loaded with an antigen or may be a miDC activated to produce IFN-α.

In various embodiments, miDCs are activated to produce IFN-α by incubating miDCs with a ligand that is recognized by a pathogen-associated pattern recognition receptor (PRR) as described herein.

The present invention provides a method for producing IFN-α using miDCs according to the present invention and comprising incubating the miDCs with an appropriate stimulus to produce IFN-α. Such a stimulus is a ligand that is recognized by a pathogen-associated pattern recognition receptor (PRR) as described herein. Preferably, the ligand is a TLR9 ligand. In various embodiments, the method for producing IFN-α using miDCs according to the present invention comprises the use of a cell population comprising miDCs. Here, in various embodiments the miDCs are purified or separated from the cell population and subsequently incubated with an appropriate stimulus to produce IFN-α. In various embodiments, the method also comprises purifying the IFN-α produced by the miDCs. The IFN-α produced by miDCs in accordance with the present invention can be purified by standard methods established and known in the art.

The present invention also provides a method for producing IL-6 using miDCs according to the present invention and comprising incubating the miDCs with an appropriate stimulus to produce IL-6. Such a stimulus is a ligand that is recognized by a pathogen-associated pattern recognition receptor (PRR) as described herein. Preferably, the ligand is at least one of a TLR2 ligand, a TLR4 ligand, a TLR7 ligand and a TLR9 ligand. In various embodiments, the TLR2 ligand is Pam3Cys. In various embodiments, the TLR4 ligand is LPS. In various embodiments, the TLR7 ligand is R837. In various embodiments, the TLR9 ligand is a CpG (for example CpG2216-ODN), or a ligand of viral origin. In various embodiments, the method for producing IL-6 using miDCs according to the present invention comprises the use of a cell population comprising miDCs. Here, in various embodiments the miDCs are purified or separated from the cell population and subsequently incubated with an appropriate stimulus to produce IL-6. In various embodiments, the method also comprises purifying the IL-6 produced by the miDCs. The IL-6 produced by miDCs in accordance with the present invention can be purified by standard methods established and known in the art.

The present invention also provides a method for producing TNF-α using miDCs according to the present invention and comprising incubating the miDCs with an appropriate stimulus to produce TNF-α. Such a stimulus is a ligand that is recognized by a pathogen-associated pattern recognition receptor (PRR) as described herein. Preferably, the ligand is at least one of a TLR7 ligand and a TLR9 ligand. In various embodiments, the TLR7 ligand is R837. In various embodiments, the TLR9 ligand is a CpG (for example CpG2216-ODN), or a ligand of viral origin. In various embodiments, the method for producing TNF-α using miDCs according to the present invention comprises the use of a cell population comprising miDCs. Here, in various embodiments the miDCs are purified or separated from the cell population and subsequently incubated with an appropriate stimulus to produce TNF-α. In various embodiments, the method also comprises purifying the TNF-α produced by the miDCs. The TNF-α produced by miDCs in accordance with the present invention can be purified by standard methods established and known in the art.

As described herein, miDCs of the present invention can stimulate T cells. Accordingly, the present invention encompasses the use of miDCs of the present invention for stimulating T cells. For stimulating T cells the miDCs are stimulated (activated) with an appropriate stimulus. In various embodiments, the miDCs are stimulated (activated) with at least one of GM-CSF, LPS and a CpG. In various embodiments, the use of miDCs of the present invention for stimulating T cells comprises the use of a cell population comprising miDCs. Here, in various embodiments the miDCs are purified or separated from the cell population and subsequently incubated with an appropriate stimulus to stimulate the miDCs. The use of miDCs of the present invention for stimulating T cells comprises incubating T cells with stimulated (activated) miDCs of the present invention either ex vivo or in vivo. Accordingly, the present invention also encompasses the therapeutic use of miDCs of the present invention for stimulating T cells in a subject in need thereof. In various embodiments, the miDCs are incubated with allogeneic T cells. In various embodiments, the miDCs are incubated with antigen-specific T cells. In various embodiments, miDC are stimulated (activated) ex vivo, and then administered to a subject in need thereof to stimulate memory T-cells. The stimulated (activated) miDC can produce high levels of T-cell stimulation.

In various embodiments, the therapeutic use of miDCs of the present invention for stimulating T cells in a subject in need thereof comprises using miDCs obtained from a host, stimulating (activating) the so-obtained miDCs, and re-introducing (administering) the so-stimulated (activated) miDCs into the host from which the miDCs to be stimulated (activated) were obtained. Here, the host is a subject in need of a treatment with miDCs for stimulating T cells.

In various embodiments concerning the use of miDCs of the present invention for stimulating T cells the miDC may be washed with a physiological buffered solution and suspended in a buffered physiological solution after stimulation (activation) with an appropriate stimulus and prior to administration to a subject in need thereof. In various embodiments, a suspension comprising at least one of $10^4$, $10^5$, $10^6$, $10^7$, $10^8$ and $10^9$ stimulated (activated) miDCs is administered to a subject in need thereof by techniques known in the art.

The invention further encompasses the activation of miDC in vivo. This can be accomplished by direct application of an activating compound, such as a CpG (e.g., CpG2216-ODN), to the bone marrow of a host. Direct application can increase the IFN-α production of the miDC in vivo. Direct application to bone marrow can be accomplished by various techniques known in the art. Thus, the present invention encompasses the use of an activating compound, such as a CpG, for the preparation of a medicament for treating bone marrow of a subject in need thereof.

The present invention encompasses reagents specific for miDC of the present invention. Accordingly, antibodies specific for any of the miDCs provided by the present invention can be generated using established techniques known in the art. For example, antibodies can be generated using miDC antigens, and then antibodies can be selected that specifically bind to miDCs, but do not bind to other cell types, such as pDC and the other cDC. Antibodies specific for any of the miDCs of the present invention encompass both monoclonal and polyclonal antibodies. Generating antibodies specific for miDC can be accomplished using standard immunological methods known in the art; see, e.g., Marks et al., 1996, New England Journal of Medicine 335:730; Mc Guiness et al., 1996, Nature Biotechnology 14:1449.

The present invention encompasses cDNA libraries specific for miDC of the present invention. Such cDNA libraries can be generated using techniques known in the art. For example, a cDNA library can be generated using RNA from miDC, and then subtracted with RNA or DNA from other types of cells, such as pDC and/or the other cDC. This provides for selecting for cDNAs of RNAs that are expressed in miDC, but not in other types of cells, such as pDC and/or the other pDC. Subtraction can be done using standard molecular biological methods; see, e.g., Weaver et al., 1999, In Molecular Embryology: Methods and Protocols, P. Sharpe and I. Mason, eds., pp. 601-609; Welcher et al., 1986, Nucleic Acids Res. 14: 10027-44.

The present invention encompasses the use of miDC for screening for drugs that either do or do not affect miDC function. In various embodiments, miDC are used to screen for drugs that inhibit or promote production of at least one of IFN-α, IL-6, and TNF-α. In various embodiments, miDC are used to screen for drugs that inhibit or promote T-cell activation by miDC. The use of miDC for screening for drugs that either do or do not affect miDC function comprises incubation of miDCs in the presence and absence of a drug. In various embodiments, the effect on the production of at least one of IFN-α, IL-6, and TNF-α is assessed by assessing the effect of the presence and absence of a test drug on the activation of miDCs with an appropriate stimulus that normally induces the production of IFN-α, IL-6, or TNF-α in miDCs as described herein elsewhere. In various embodiments, the effect on the activation of T cells is assessed by assessing the effect of the presence and absence of a test drug on the activation of miDCs with an appropriate stimulus that normally activate miDCs as described herein elsewhere.

The present invention provides a pharmaceutical composition (medicament) comprising miDCs of the present invention. In various embodiments, the pharmaceutical composition is an immunotherapeutic composition. The present invention also encompasses a pharmaceutical composition comprising an immunotherapeutic agent obtained by a method according to the present invention. As described herein, in various embodiments a miDC of the present invention can be used as an immunotherapeutic agent. In various embodiments, the immunotherapeutic agent of the present invention is a vaccine. This applies in particular to antigen-loaded APmiDCs provided by the present invention.

The present invention encompasses the use of miDCs of the present invention for the preparation of a pharmaceutical composition (medicament). The present invention also encompasses the use of miDCs of the present invention for the preparation of an immunotherapeutic agent. The present invention further encompasses the use of miDCs of the present invention for the preparation of a vaccine.

The present invention provides a method for preparing an immunotherapeutic agent, comprising the steps of (a) providing bone marrow-derived non-plasmacytoid dendritic cells (non-pDCs) that are CD11b$^{-/lo}$; and (b) modifying ex vivo the non-pDCs of step (a) such that they are loaded with one or more antigens. In various preferred embodiments, the method further comprises incubating the antigen-loaded non-pDCs of step (b) with an activator of dendritic cell maturation. In various embodiments, the activator of dendritic cell maturation is at least one of a cytokine or an interferon (including type I IFN and IFN-gamma), growth factors (including GM-CSF, M-CSF, SCF, Flt3-L, G-CSF, LIF, Oncostatin M, and IL-34), TNF family members (including, e.g. TNF-α, TNF-β, CD40L, CD27L, CD30L, and 4-1BBL), TGF family members (including, e.g., TGF-α, TGF-β, Nodal), interleukins (including, e.g., IL-1a, IL-1b, IL-2, IL-3, IL-4, IL-6, IL-7, IL-9, IL-10, IL-11, IL-12, IL-13, IL-15, IL-17, IL-18, IL-21, IL-22, IL-23, IL-25, IL-31, IL-33, IL-35). In various other embodiments, the activator of dendritic cell maturation is a pattern recognition receptor, preferably at least one of a TLR-ligand (including, e.g., ligands for TLR2, -3, -4, -5, -7, -8, -9, -10, -11, -12, and -13), Rig-like helicases (including Rig-I and MDA5 ligands), cytoplasmic DNA receptor ligands (including, e.g., ligands for DAI, STING), PKR, and Nod-like receptors (including, e.g., ligands for NALP1, NALP1b, NALP3, IPAF, NAIP, NOD1, NOD2, CARD).

In various further embodiments, the activator of dendritic cell maturation is a c-type lectin, preferably at least one of CD205, CD206, CD209, Clec1B, Clec2, Clec3B, Clec4F, Clec6A, Clec7A, Clec9A, Clec11A, Clec12A, Clec13D, and Clec13E.

The immunotherapeutic agents provided by the present invention are used for treating a subject, preferably a human, in need thereof.

In various embodiments, treating a subject according to the present invention comprises administering at least $10^4$ miDC according to the present invention. Thus, in various embodiments, treating a subject according to the present invention comprises administering at least $10^4$ in vitro activated miDCs.

Preferably, treating a subject according to the present invention comprises administering at least $10^5$ miDC according to the present invention. More preferably, treating a subject according to the present invention comprises administering at least $10^6$ miDC according to the present invention. Still more preferably, treating a subject according to the present invention comprises administering at least $10^7$ miDC according to the present invention. Even more preferably, treating a subject according to the present invention comprises administering at least $10^8$ miDC according to the present invention. In still more preferred embodiments, treating a subject according to the present invention comprises administering at least $10^9$ miDC according to the present invention.

The present invention encompasses ex vivo activation of miDCs, including a cell population comprising miDCs, to produce IFN-α as described herein and subsequent administration of the so-activated miDCs to a subject in need thereof. Specifically, a population of miDCs induced to produce IFN-α by contacting ex vivo miDCs or a population of miDCs with an appropriate stimulus, i.e. a ligand/stimulus inducing the production of IFN-α in miDCs as described herein elsewhere, may be administered to a subject in need thereof. Accordingly, the present invention provides a method for inducing a reaction against an infectious disease or cancer in vivo comprising contacting ex vivo miDCs of the present invention with an appropriate ligand/stimulus inducing the production of IFN-α in the miDCs and introducing them into a subject suffering from an infectious disease or cancer. In other words, the present invention provides a method for the prevention and/or treatment of a subject suffering from an infectious disease or cancer comprising administering to said subject IFN-α producing miDCs generated by an ex vivo method for inducing the production of IFN-α in a population of miDCs, said method comprising contacting ex vivo miDCs according to the present invention with a ligand/stimulus inducing the production of IFN-α in the miDCs. In various embodiments, the present invention provides a method for the prevention and/or treatment of an infectious disease or cancer comprising: (a) providing a subject suffering from an infectious disease or cancer; (b) obtaining miDCs from said subject; (c) contacting said miDCs ex vivo with a stimulus inducing the production of IFN-α in the miDCs to generate a population of miDCs producing IFN-α; and (d) re-introducing said population of IFN-α producing miDCs into said subject so as to induce an in vivo therapeutic reaction against the infectious disease or cancer. Preferably, the population of miDCs is washed prior to re-introducing into the subject. In another preferred embodiment, the population of IFN-α producing miDCs is resuspended in media suitable for administration to the subject in need thereof, preferably in a buffered physiological solution. The populations of IFN-α producing miDCs may be re-introduced to the subject by a number of well-known approaches like, for example, intravenous injection.

In all embodiments according to the present invention, which concern and/or include contacting ex vivo miDCs with a ligand/stimulus for inducing the production of IFN-α in miDCs and/or a population of cells comprising miDCs, preferably Flt3-ligand- and/or M-CSF receptor ligand-pretreated miDCs may be contacted ex vivo with an appropriate stimulus inducing the production of IFN-α in the miDCs. This means that a Flt3-ligand and/or a M-CSF receptor ligand may be administered to a subject prior to obtaining the miDCs from said subject for inducing the production of IFN-α by contacting ex vivo the obtained miDCs with a ligand/stimulus inducing the production of IFN-α in miDCs. This pretreatment with a Flt3-ligand and/or a M-CSF receptor ligand may provide for increasing the formation/level of miDCs in said subject prior to obtaining such pretreated miDCs from said subject for contacting ex vivo said pretreated miDCs with a ligand/stimulus inducing the production of IFN-α in miDCs.

In the context of obtaining miDCs from a subject for contacting ex vivo miDCs with a stimulus inducing the production of IFN-α in miDCs and/or a population of cells comprising miDCs, methods for obtaining/isolating miDCs from a subject are well-known to the person skilled in the art. In the present invention, the terms "obtaining miDCs from a subject" and "isolating miDCs from a subject" are used interchangeably.

In various embodiments according to the present invention, which concern/include contacting ex vivo miDCs with a stimulus inducing the production of IFN-α in miDCs and/or in a population of cells comprising miDCs, miDCs obtained/isolated from a subject may be further incubated with at least one of a TLR2-, TLR4-, TLR9-, TLR10-, and CD40-ligand, preferably Pam3Cys, LPS, CpG-ODN, or a CD40-ligand. This incubation may increase the expression of IFN-α. In various embodiments, the miDCs obtained/isolated from a subject may be further incubated with a cytokine, preferably IL-3, GM-CSF, IL-4, or IFN-gamma (IFN-γ).

In various embodiments of the present invention, the ligand/stimulus recognized by a pattern recognition receptor inducing the production of IFN-α in miDCs is a ligand/stimulus recognized by a pattern recognition receptor (PRR), preferably a pathogen-associated PRR. In other words, in various embodiments of the present invention the pattern recognition receptor is a pathogen associated pattern recognition receptor. In various embodiments of the present invention, the ligand/stimulus recognized by a pathogen-associated pattern recognition receptor is a ligand recognized by a cell surface, endosomal and/or cytoplasmic pathogen-associated pattern recognition receptor. In other words, in various embodiments of the present invention the pathogen associated pattern recognition receptor is a cell surface, endosomal and/or cytoplasmic pathogen-associated pattern recognition receptor. The immune system recognizes pathogens or other forms of danger by means of "pattern-recognition receptors" (PRR) which bind to certain structures (patterns) of molecules and trigger signaling into the cells. They are located either on the outer membranes, in endosomes or within the cytoplasm of cells. Among the PRRs different families have been described and are known to the person skilled in the art. Each family shows certain similarities in structure or the use of adaptor molecules used for signaling among.

The best examined examples of those PRR families are the family of Toll-like receptors (TLRs), which shows as structural similarity the leucine-rich repeats and the so called TIR domains. Accordingly, in various embodiments of the present invention the PRR is preferably a PRR of the family of Toll-like receptors (TLRs). These signal either via the adaptor molecule MyD88 or TRIF.

Another example of a PRR family is the Rig-like Helicases with RIG-I and MDA5 as active members. Accordingly, in various embodiments of the present invention the PRR is preferably a PRR of the family of Rig-like Helicases with RIG-I and MDA5 as active members. Those receptors are located in the cytoplasm and signal via the adaptor molecule CARDIF, also known as IPS-1, VISA or MAVS. They are known to recognize certain different form of RNA.

Still another family of PRR is the NOD-like receptors, which induce certain caspases and thus are linked to the induction of active IL-1 and IL-18. Accordingly, in various embodiments of the present invention the PRR is preferably a PRR of the family of NOD-like receptors.

In various embodiments of the present invention the PRR is preferably a cytoplasmic DNA recognition receptor, which recognizes DNA viruses. Here, the DNA virus is preferably an Adenoviruses, Poxviruses or Herpesviruses.

Often pathogens harbor different pattern, e.g. gram negative bacteria have LPS which is recognized by TLR4, but they also contain DNA and RNA which could be recognized by TLR9 or TRL7 respectively. On the other hand could some pathogens be recognized by the same pattern via different PRRs often expressed by different cell types, e.g. the DNA virus HSV-1 is recognized by plasmacytoid DC via TLR9 whereas other cell types such as macrophages recognize it via an unknown receptor in the cytoplasm. Another example is the recognition of certain ssRNA viruses such as Influenza or Sendai virus, which are recognized by plasmacytoid DC via TLR7, whereas certain conventional DC use RIG-I for recognition. Accordingly, in various embodiments of the present invention the ligand recognized by a PRR is preferably a ligand recognized by the same pattern via different PRRs.

Numerous review articles list the ligand and receptor interaction of PRR, e.g. Akira 2009, Pathogen recognition by innate immunity and its signaling. Proc. Jpn. Acad. Ser. B. Phys. Biol. Sci. 85(4):143-56; and Latz and Fitzgerald 2008, Innate immunity: sensing and signalling. Nature Reviews Immunology. Poster April 2008, Vol. 8(4). The disclosure of said references with respect to the specific ligand and receptor interaction of PRR is incorporated herein by reference. In various embodiments of the present invention, the ligand and receptor interaction of PRR is as described in said references. That is, the ligand and receptor interaction of PRR described in Akira 2009 and Latz and Fitzgerald 2008 from part of the present application and define preferred embodiments of the present invention by reference.

In the present invention, the ligand recognized by a pattern recognition receptor according to the present invention is preferably a TLR3 ligand, a TLR7 ligand, a TLR8 ligand, or a TLR9 ligand.

In preferred embodiments, the pattern recognition receptor is at least one of a TLR-ligand (including, e.g., ligands for TLR2, -3, -4, -5, -7, -8, -9, -10, -11, -12, and -13), Rig-like helicases (including Rig-I and MDA5 ligands), cytoplasmic DNA receptor ligands (including, e.g., ligands for DAI, STING), PKR, and Nod-like receptors (including, e.g., ligands for NALP1, NALP1b, NALP3, IPAF, NAIP, NOD1, NOD2, CARD).

One of the properties of the miDCs of the present invention is their ability to uptake exogenous proteins by endocytosis, which are then processed and presented as peptide epitopes on their surface in conjunction with MHC class I or MHC class II molecules.

These antigen-presenting miDCs of the present invention can be recognized by cytotoxic T cells. This property is extremely important when tumor cell antigens are applied in form of tumor lysates or apoptotic bodies added exogenously. An antigen-presenting miDC (APmiDC) according to the present invention is capable of activating T cells, preferably naive T cells.

The present invention provides a composition for stimulating the immune system in a subject in need thereof, wherein the composition comprises miDCs according to the present invention that expresses a cell-surface antigen. The present invention provides means and methods of vaccinating subjects against pathogens and tumors in which the immune response relies primarily on a T cell rather than an antibody-based immune response. The use of the miDCs provided by the present invention in eliciting an antigen-specific immune response in a subject in need thereof according to the present invention involves administering to the subject an amount of miDCs of the present invention as antigen-presenting cells (APmiDCs) sufficient to induce an immune response in a subject, wherein the APmiDCs express an antigen as described herein elsewhere. Such an amount is referred herein as an effective amount.

In various embodiments, the miDCs of the present invention may be loaded with one or more antigens. Thus, the miDCs of the present invention encompass antigen-loaded or antigen-pulsed miDCs. Accordingly, these antigen-pulsed miDCs or antigen-loaded miDCs are antigen-presenting miDCs. The present invention provides such antigen-presenting miDCs (APmiDCs). As used herein, antigen-loaded or antigen-pulsed miDCs include miDC of the present invention, which have been exposed to an antigen. The miDC of the present invention can be loaded with antigens by many techniques known in the art. In one embodiment, miDC can be loaded with soluble antigen by incubating ("pulsing") the antigen and miDC in culture for a sufficient time to allow the miDC to uptake the antigen, and to initiate antigen processing. For example, miDC may be pulsed with antigen for about 1 to 2 hours at 37° C.; see, e.g., Celluzi et al., 1996, J. Exp. Med. 183:283-7; Hu et al., 1996, Cancer Res. 56:2479-2483. In general, an APmiDC according to the present invention may become antigen-loaded in vitro, e.g., during culture in the presence of an antigen. The APmiDC may also be loaded in vivo by exposure to an antigen. An "antigen-loaded APmiDC" according to the present invention may be prepared in accordance with two known traditional ways of preparing "antigen-loaded antigen-presenting cells (APCs)", namely: (1) small peptide fragments, know as antigenic peptides, are "pulsed" directly onto the outside of the APCs; or (2) the APC is incubated with whole proteins or protein particles which are then ingested by the APC. These proteins are digested into small peptide fragments by the APC and are transported to and presented on the APC surface.

The above described known ways of antigen loading or antigen pulsing of APCs are encompassed by the present invention for antigen loading or antigen pulsing of miDCs provided by the present invention for use as "antigen-loaded APmiDC" or "antigen-pulsed APmi DC". An "antigen-loaded APmiDC" or "antigen-pulsed APmiDC" according to the present invention may also be called "antigen-activated APmiDC".

Further encompassed by the present invention is loading of miDCs according to the present invention by immune complex-mediated uptake of an antigen by dendritic cells as described in U.S. 2002/0155108. The corresponding disclosure of U.S. 2002/0155108 concerning immune complex-mediated uptake of an antigen by dendritic cells is incorporated herein by reference.

In addition, the antigen-loaded APC can also be generated by introducing a nucleic acid encoding an antigen into the cell. As used herein, a miDC expressing a cell-surface antigen is a miDC that was beforehand transfected with one or more nucleic acid constructs each of which encoding one or more identified antigens according to the present invention. In various embodiments, RNA encoding an antigen may be delivered into a miDC, such as by electroporation or by incubating the RNA in the presence of a cationic lipid, and then contacting the RNA-lipid complex with the miDC; see, e.g., Boczkowski et al., 1996, J. Exp. Med. 184: 465-72. In other embodiments, retroviral vectors encoding an antigen may be transduced into a miDC; see, e.g., Szabolcs et al., 1997, Blood, 90:2160-7; Ashley et al., 1997, J. Exp. Med. 186: 1177-82. Similarly, adenoviral vectors or vaccinia virus vectors, such as MVA vectors, can been used to transduce miDC to express and present one or more antigens.

In various embodiments, the miDC provided by the present invention may be genetically modified using a vector, preferably a viral vector, more preferably an adeno-associated virus (AAV) vector, which allows for the expression of a specific protein by the miDC. The protein which is expressed by the miDC may then be processed and presented on the cells surface on an MHC receptor. The modified miDC may then be used as an immunogenic composition or immunotherapeutic agent to induce tolerance to the protein in a subject in need thereof in accordance with the present invention. In various embodiments, genetically modifying the miDCs according to the present invention includes using a viral vector as vehicle for introducing heterologous gene(s) encoding an antigen according to the present invention into the miDC. Preferably, the viral vector is an AAV vector. In particular, the viral vector is operably linked to at least one heterologous gene, which encodes an antigen according to the present invention.

Thus, in various embodiments, the miDCs used for stimulating the immune system of a patient in need thereof are miDCs comprising at least one viral vector, preferably an AAV vector, comprising at least one heterologous gene selected from the group consisting of a gene encoding an antigen according to the present invention, a gene encoding a cytokine and combinations of one or more genes thereof, whereby the heterologous gene is expressed in the miDCs and the subject's immune system is stimulated by the stimulation of the subject's T cell response.

As used herein, various methods can be used for transfecting a polynucleotide into a host cell. The methods include, but are not limited to, calcium phosphate precipitation, lipofection, particle bombardment, microinjection, and electroporation.

The miDCs of the present invention express the gene encoding the antigen, process the antigen and present this antigen as an antigenic epitope for T-cell priming. But even a genetically altered miDC of the present invention that carries a heterologous gene encoding a cytokine is useful for treating cancers or other diseases that would benefit from cytokine treatment because the expression of cytokines by the miDCs stimulates the basal level of tumor cell recognition and enhanced the immune response. Additionally, these genetically altered miDCs also provided by the present invention are useful to stimulate the patient's own T-cells in vivo and/or these genetically altered miDCs are useful to stimulate T-cells in vitro, and then these primed T-cells are administered to the patient to stimulate the patient's immune system via adoptive immunotherapy.

After loading with an antigen, the APmiDC of the present invention, including genetically modified or genetically altered miDCs as described above, can be administered to a subject in need thereof. In various embodiments, the APmiDCs may be washed with a physiological buffered solution and suspended in a buffered physiological solution prior to administration to a subject in need thereof. In various embodiments, a suspension comprising at least one of $10^4$, $10^5$, $10^6$, $10^7$, $10^8$ and $10^9$ APmiDCs is administered to a subject in need thereof by techniques known in the art.

The APmiDCs of the present invention that express the antigen may be introduced into the body of a subject, where they migrate to lymphoid tissue (such as lymph nodes or spleen), and produce high cytoplasmic levels of the immunogenic antigen. When the APmiDCs die in the lymphatic tissue, the antigen efficiently induces T cell immunity via cross-priming.

In various embodiments, the preparation of APmiDCs comprises using miDCs obtained from a host, loading the so-obtained miDCs with one or more antigens, and re-introducing (administering) the so-prepared APmiDCs into the host from which the miDCs to be loaded with one or more antigens were obtained. Here, the host is a subject in need of stimulating its immune system.

In various embodiments, the miDCs can be administered to a subject in need thereof in an activated or inactivated state. In various embodiments, the miDCs administered to a subject in need thereof may be further activated by a ligand recognized by a cytokine and/or pattern recognition receptor according to the present invention.

The use of miDCs provided by the present invention in eliciting an antigen-specific immune response in a subject in need thereof according to the present invention provides several advantages over known methods of inducing a T cell response.

The immunotherapeutic agents and compositions of the present invention can be administered to a subject (e.g., a human) to stimulate the subject's immune system. This subject may need an immune stimulation due to an infectious disease, or susceptibility to an infectious disease, due to a cancer disease, or due to a predisposition to develop a cancer disease. Preferably, the infectious disease is at least one of a viral infection, a bacterial infection, a parasitic infection, and a fungal infection.

Stimulation of the immune system with an APmiDC according to the present invention results in enhancement of the subject's immunity against an infectious disease or cancer characterized by abnormal expression of a cell surface antigen. Abnormal expression means that the cell surface antigen (i) is not expressed in normal tissue, (ii) is expressed at a much higher level in diseased cells of a given tissue type than in normal tissue of the same type, or (iii) is modified (e.g., phosphorylated) differently in diseased cells of a given tissue type than in normal cells of the same type. Enhancement of immunity entails enhancement of the immune system's cell-mediated or humoral functions, or both.

As used herein, the antigen may be a self-antigen or an antigen associated with a disease selected from a viral infection or cancer, preferably a viral infection, a bacterial infection, a fungal infection, or a parasite infection. The antigen may be a therapeutic protein exogenously produced to achieve a pharmacological or biological effect in a subject in need thereof.

In various embodiments, the miDCs of the present invention used as APmiDCs present a multiplicity of viral antigens. In various embodiments, the miDCs of the present invention used as APmiDCs present a multiplicity of bacterial antigens. In various embodiments, the miDCs of the present invention used as APmiDCs present a multiplicity of fungal antigens. In various embodiments, the miDCs of the present invention used as APmiDCs present a multiplicity of parasite antigens. In various embodiments, the miDCs of the present invention used as APmiDCs present a multiplicity of tumor antigens.

In various embodiments, the miDCs of the present invention used as APmiDCs are cultured ex vivo in growth medium with or without any cytokines before loading the miDCs with one or more antigens according to the present invention. In various embodiments, the miDCs of the present invention used as APmiDCs are matured by maturation factors after loading of the antigen(s).

In various embodiments, the antigen is a tumor associated antigen (TAA). There are two major types of TAA: unique antigens, present only in very few tumors and therefore not useful as general targets, and shared or common TAAs, present in many tumors. The following three major groups of shared antigens are potential targets for immunotherapy and have all been shown to induce generation of cytotoxic T lymphocytes: cancer/testis antigens (CT antigens), tumor over-expressed antigens, and lineage-specific differentiation antigens. These three groups of antigens are encompassed by the present invention.

CT antigens are encoded by cancer or germ line specific genes, representing one of the largest groups of shared tumor-associated antigens. CT antigens were originally discovered in melanomas but have also been found in many other human malignancies. Among normal tissue they are only expressed in testis and in some cases in placenta. Normal cells expressing these antigens lack expression of MHC molecules and therefore these antigens are normally not accessible for recognition by T lymphocytes. This makes CT antigens very attractive targets for specific cancer immunotherapy. Many CT antigens can be grouped into subfamilies that include several members. They are the MAGE-A, MAGE-B, MAGE-C, GAGE, LACE and SSX subfamilies. For the other antigens only one individual member has been discovered so far. These are the BAGE, SCP-1, TSP-50, TRAG-3, SAGE, IL-13R alpha, CT9 and CTp11 antigens. Each of these CT antigens may be used as potential targets for immunotherapy in accordance with the purpose of the present invention. Accordingly, in various embodiments, the antigen is selected from the MAGE-A, MAGE-B, MAGE-C, GAGE, LACE and SSX subfamilies. In various other embodiments, the CT antigens comprise antigens selected from SCP-1, TSP-50, TRAG-3, SAGE, IL-13R alpha, and CTp11.

One condition for employment of melanoma cell-based compositions or vaccines according to the present invention is the presence in a host of a malignancy at advanced stages of disease. Another condition could be the presence of a primary tumor, and in this case the aim of treatment is not only to induce rejection of the primary tumor, but also to prevent development of metastases, since a group of CT antigens is predominantly expressed in metastases. Yet another condition could be removal of primary or metastatic tumor by other means (e.g., surgery, irradiation), and in this case the aim of treatment is the prevention of tumor recurrence.

Tumors that express several CT antigens have higher chances of being rejected or restricted in growth than tumors that have no or only one CT antigen. Therefore, determination of expression of CT antigens in tumor biopsy may be of significance in predicting the effectiveness of employment of a universal melanoma cell-based vaccine.

Tumor over-expressed antigens in accordance with the present invention comprise antigens like CEA, p53, HER-2/Neu, MUC-1 and alpha-fetoprotein.

Lineage specific antigens in accordance with the present invention comprise the melanocyte differentiation antigens gp100, Melan-A/MART-I, Tyrosinase, TRP-1, TRP-2, MCI R, AIM-1 and the prostate-associated antigens PSA (prostate specific antigen), PSMA (prostate specific membrane antigen), PAP (prostate associated phosphatase), and PSCA (prostate stem cell antigen).

Tumor antigens encompassed by the present invention are further discussed in greater detail in WO 02/061113, WO 03/025002, WO 03/024994, WO 03/024304, and WO 03/024302.

An object of the present invention may also be a method for increasing the level of miDCs in a subject suffering from an infectious disease or cancer comprising administering to a subject in need thereof Flt3-ligand (FL) or a M-CSF receptor ligand. In other words, the present invention may provide FL or a M-CSF receptor ligand for use in increasing the level of miDCs in a subject suffering from an infectious disease or cancer. FL or a M-CSF receptor-ligand may be administered to the subject at a dosage or amount sufficient or effective to increase the level of miDCs according to the present invention in said subject. The M-CSF receptor ligand may be M-CSF or IL-34. In a method for increasing the level of miDCs in a subject suffering from an infectious disease or cancer, a nucleic acid or analog thereof according to the present invention may be administered to the subject in addition to FL or a M-CSF receptor ligand. Said additional administration of a nucleic acid or analog thereof according to the present invention may stimulate the production of IFN-α in the subject suffering from an infectious disease or cancer.

The present invention furthermore provides a method for inducing the production of IFN-α in a population of miDCs comprising contacting ex vivo miDCs with a ligand recognized by a pathogen-associated PRR, preferably a nucleic acid or analog thereof according to the present invention. In particular, for inducing said production of IFN-α ex vivo, miDCs are obtained from a subject prior to contacting said miDCs with an appropriate ligand recognized by a pathogen-associated PRR. In the method for inducing the production of IFN-α in a population of miDCs according to the present invention, the subject from whom the miDCs are obtained is preferably a subject in need of a treatment with miDCs induced to produce large amounts of IFN-α. Thus, the subject may be a subject in need of a prevention and/or treatment of an infectious disease, preferably a viral infection, or cancer. More preferably, the miDCs may preferably be obtained from a subject suffering from a persistent viral infection, more preferably a viral infection of the liver or a Herpes virus infection, still more preferably a Hepatitis virus infection. Following incubation ex vivo with a ligand recognized by a pathogen-associated PRR, preferably a nucleic acid or analog thereof according to the present invention, the miDCs are harvested and resuspended in appropriate media for therapy, i.e. for being reintroduced into the subject from whom they were derived. Thus, in the method for inducing the production of IFN-α in a population of miDCs according to the present invention the miDCs are preferably autologous miDCs. The re-introduction to the subject in need thereof may be carried out by a number of commonly known approaches, like for example intravenous injection. Furthermore, the population of miDCs induced for production of IFN-α may be re-introduced in a variety of pharmaceutical formulations. Thus, the present invention provides a population of IFN-α producing miDCs obtainable by a method for inducing the production of IFN-α in a population of miDCs according to the present invention as well as a pharmaceutical composition comprising said population of IFN-α producing miDCs.

As used herein, the infectious disease is preferably a viral infection. More preferably, in all therapeutic applications according to the present invention the viral infection is a persistent viral infection. Still more preferably, the persistent viral infection is a viral infection of the liver or a Herpes virus infection. In a specifically preferred embodiment, said viral infection of the liver is a Hepatitis virus infection. Accordingly, in the methods for the prevention and/or treatment of an infectious disease or cancer in a subject in need thereof, preferably the viral infection is a persistent viral infection, more preferably a viral infection of the liver or a Herpes virus infection, and still more preferably a Hepatitis virus infection. In the present invention, a Hepatitis virus infection includes a Hepatitis A virus infection, a Hepatitis B virus infection, a Hepatitis C virus infection, a Hepatitis D virus infection and a Hepatitis E virus infection, wherein the Hepatitis virus infection preferably is a Hepatitis C virus infection. In another preferred embodiment, in the present invention the persistent viral infection is a retroviral infection.

The subject according to the present invention includes animals and human. In accordance with the present invention, a "subject" shall mean a human or vertebrate animal including a dog, cat, horse, cow, pig, sheep, goat, chicken, monkey, rat, and mouse. In the various embodiments according to the present invention, the subject is preferably human.

In various preferred embodiments of the present invention, the subject suffering from cancer is a subject suffering from a tumor disease. Preferably, the tumor disease is a carcinoma, i.e. a cancer or tumor of the epithelial cells or epithelial tissue in a subject. Preferably the carcinoma is a squamous cell carcinoma or an adenocarcinoma. More preferably, the carcinoma is squamous cell lung cancer.

In the methods and therapeutic applications described above, a nucleic acid or analog thereof according to the present invention can be used alone or in combination with one or more other anti-cancer or anti-tumor therapeutic uses and methods, wherein such therapeutic uses and methods are preferably selected from anti-tumor chemotherapy and immunotherapy. Thus, a nucleic acid or analog thereof according to the present invention targeting miDCs according to the present invention, i.e. a nucleic acid that is capable of stimulating or inducing IFN-α production in miDCs, can be administered prior to, along with or after administration of a chemotherapy or immunotherapy to increase the responsiveness of the malignant cells to subsequent chemotherapy or immunotherapy.

Also provided by the present invention is a method for the production of IFN-α in a subject comprising administering to said subject a nucleic acid or analog thereof according to the present invention targeting miDCs according to the present invention.

The present invention may also provide a combined preparation comprising a nucleic acid or analog thereof targeting miDCs and a ligand enhancing nucleic acid-based IFN-α production. The ligand enhancing nucleic acid-based IFN-α production may be Flt3-ligand, a M-CSF receptor ligand, a TLR2 ligand, a TLR4 ligand, a TLR9 ligand, a TLR10 ligand, a TLR11 ligand, IL-3, GM-CSF, IL-4, or IFN-γ.

The present invention provides a method for producing IFN-α and/or generating or obtaining a population of IFN-α producing miDCs, comprising the steps of: (a) providing a population of cells comprising miDCs according to the present invention; and (b) contacting the miDCs with a ligand that is recognized by a pathogen-associated PRR as described herein, preferably a nucleic acid or analog thereof according to the present invention. Contacting the miDCs with a ligand recognized by a pathogen-associated PRR stimulates the production of IFN-α in the miDC.

In various preferred embodiments, the above-described methods further comprise a step of identifying and/or detecting IFN-α produced by the miDCs stimulated with a ligand recognized by a pathogen-associated PRR. In various preferred embodiments, the above described methods still further comprise a step of isolating and/or separating IFN-α produced by the miDCs. In other preferred embodiments, the above described methods further comprise a step of identifying and/or isolating and/or separating IFN-α producing miDCs.

The IFN-α produced by the miDCs according to the present invention can be detected and quantitated by techniques well-known in the art. The IFN-α produced by the miDCs in accordance with the present invention can also be collected, isolated, and purified by conventional biochemical techniques.

In a preferred embodiment of the above described methods for producing IFN-α and/or generating or obtaining a population of IFN-α producing miDCs, the population of cells comprises more than at least one of 10%, 20%, 30%, 40%, 50%, 60%, 70%, 75%, 80%, 85%, 90%, 95%, 96%, 97% 98% and 99% miDCs according to the present invention.

The present invention provides a population of IFN-α producing miDCs according to the present invention or a cell line of an IFN-α producing miDC, obtainable by the above described methods for generating or obtaining a population of IFN-α producing miDCs.

The present invention further provides kits useful for introducing antigen-encoding cDNA into miDCs for generating APmiDCs in accordance with the present invention, for example for transfecting miDCs with a nucleic acid encoding one or more desired antigens. For example, a kit useful for transfecting miDCs with one or more antigens includes an appropriate amount of the one or more antigens as well as, optionally, any reagents useful for carrying out the transfection. In various embodiments the kit further includes instructions for using the kit, and/or frozen aliquots of miDCs of the present invention.

Thus, in various embodiments, the present invention provides a kit including a container of one or more antigens (a sufficient amount for either a single use or multiple uses), and instructions for introducing the one or more antigens into miDCs, for example by transfection. The instructions can be in written form, or can be provided in an electronic format, such as on a diskette or a CD ROM. Instructions can also be provided in the form of a video cassette.

Further embodiments of the disclosure include kits useful for inducing a T cell response in a subject. For example, a kit useful for inducing a T cell response in a subject includes an appropriate amount of miDCs transfected with one or more antigens as described herein as well as, optionally, any instructions for using the kit.

In therapeutic applications according to the present invention, the miDCs can be suspended in an appropriate diluent, at a concentration of from about 0.01 to about $5 \times 10^6$ cells/ml. Suitable excipients for injection solutions are those that are biologically and physiologically compatible with the miDCs and with the recipient, such as buffered saline solution or other suitable excipients. The compositions for administration according to the present invention, including any pharmaceutical compositions and vaccines, can be formulated, produced and stored according to standard methods complying with proper sterility and stability.

As used herein, the dosage of the miDCs to be administered (i.e., the effective amount), including APmiDCs according to the present invention, varies within wide limits and may be adjusted to the specific requirements pertaining to a subject/recipient in each particular case. The number of cells used depends on the weight and condition of the subject/recipient, the number and/or frequency of administration(s), and other variables known to those of skill in the art.

Between about $10^2$ and about $10^{13}$ miDCs per 100 kg body weight can be administered to a subject in need thereof. In various embodiments, between about $1.5 \times 10^6$ and about $1.5 \times 10^{12}$ cells are administered per 100 kg body weight. In various other embodiments, between about $1 \times 10^9$ and about $5 \times 10^{11}$ cells are administered per 100 kg body weight. In various other embodiments, between about $4 \times 10^9$ and about $2 \times 10^{11}$ cells are administered per 100 kg body weight. In various other embodiments, between about $5 \times 10^8$ and about $1 \times 10^{10}$ cells are administered per 100 kg body weight.

As used herein, cross-priming is a specific capacity of antigen presenting cells (APC) that involves the acquisition of exogenous antigens from apoptotic or dead cells in the periphery and the migration to secondary lymphoid organs, where APC, for example dendritic cells, undergo apoptosis and are taken up by secondary APC. These APC reprocess the antigen and present it to T cells. For vaccination purposes, part of the pathway can be bypassed by directly introducing (for example by transfection or injection) an antigen to an antigen presenting cell (APC), for example a dendritic cell, and allowing the cell to migrate to the spleen or lymph node. Secondary APCs phagocytose dying primary APC and present the antigen to T cells (for review, see Zhou et al., "Current methods for loading dendritic cells with tumor antigen for the induction of antitumor immunity", J. Immunother. 25(4): 289-303, 2002).

The term "effective amount" in accordance with the present invention refers to the amount necessary or sufficient to realize a desired effect, or to effect a beneficial or desired result, in particular a medical and/or biological one. An effective amount can be administered in one or more administrations, application or dosages. The effective amount can be an amount that is effective alone, or in combination with other agents (such as other anti-infective or anti-neoplastic chemotherapeutic agents).

As used herein, an immune response is a response of a cell of the immune system, such as a B cell, T cell, or monocyte, to a stimulus. In various embodiments, the response is specific for a particular antigen (an "antigen-specific response"). An immune response can be a humoral (antibody or B cell response) or cellular (cell mediated or T cell response). In various embodiments, an immune response is a T cell response, such as a $CD4^+$ T cell response or a $CD8^+$ T cell response.

As used herein, a pharmaceutical composition or medicament is a composition capable of inducing a desired therapeutic or prophylactic effect when properly administered to a subject or a cell.

The pharmaceutical compositions of the present invention may comprise pharmaceutically acceptable carriers or pharmaceutically acceptable adjuvants. As used herein, the term "pharmaceutically acceptable diluent or carrier" is intended to include substances that can be co-administered with the active compound of the medicament and allows the active compound to perform its intended function. Examples of such carriers include solutions, solvents, dispersion media, delay agents, emulsions and the like. The uses of such media for pharmaceutically active substances are well known in the art. Any other conventional carrier suitable for use in the present invention falls within the scope of the instant invention. Thus, the pharmaceutically acceptable carriers and adjuvants useful in this disclosure are conventional. For example, Remington's Pharmaceutical Sciences, by E. W. Martin, Mack Publishing Co., Easton, Pa., 15th Edition (1975), describes compositions and formulations suitable for pharmaceutical delivery. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Examples of tumors according to the present invention include sarcomas and carcinomas, including, but not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma oligodendroglioma, menangioma, melanoma, neuroblastoma and retinoblastoma).

As used herein, the term "cancer antigen" means an antigenic molecule that is expressed primarily or entirely by cancer cells, as opposed to normal cells in an individual bearing the cancer. The terms "cancer antigen" and "tumor antigen" are used herein interchangeably.

As used herein, the pathogen-associated PRR may at least one of a cell surface, endosomal and cytoplasmic pathogen-associated PRR.

As used herein, the term "ds" is equally used for the terms "double-strand" and "double-stranded", respectively. Likewise, the term "ss" is equally used for the terms "single-strand" and "single-stranded".

Poly IC is a mismatched ds RNA with one strand being a polymer of inosinic acid, the other a polymer of cytidylic acid. Poly IC is a synthetic double-strand RNA and, thus, can be considered as a synthetic analog of ds RNA. Poly IC is a common tool for scientific research on the immune system. In a preferred embodiment, the nucleic acid or analog thereof according to the present invention is poly IC. However, further synthetic analogs of nucleic acids are equally suitable according to the present invention as, for example, polyadenylic-polyuridylic acid (Poly AU), which is a synthetic ds RNA, signalling exclusively via TLR3. Likewise, equally suitable is poly (ICLC), which is a poly IC complexed with carboxymethylcellulose and poly L-lysine, or poly (dA:dT), which is a synthetic ds DNA of poly (dA-dT)*poly (dA:dT) complexed with liposomes.

BRIEF DESCRIPTION OF THE DRAWINGS

FIG. 7A-C depict proliferative capacity of miDC. A. miDC were labelled with CFSE, incubated with CpG-2216, R837, GM-CSF, MVA-BN® or media and analysed by FACS 24 h later for loss of CFSE fluorescence. All traces were overlayed on each other. Shown are the overlayed results for GM-CSF, R837 and media. All traces similarly showed no evidence of miDC proliferation. Data are of one experiment of DC purified from BM of 20 pooled mice and are representative of two experiments B. CFSE-labelled miDC were spiked into FLDC cultures and analysed for surface expression of CD11c and CD45R, relative to the undivided peak 1 or division peaks 2 or 3, 4 or 5 days later. Data are of one experiment of miDC purified from BM of 12 pooled C57BL/6 mice and are representative of two separate experiments. C. A third experiment using Ly5.1 miDC gave similar results with respect to surface phenotype, with CD45R expression essentially absent by day 6.

Figure 1:
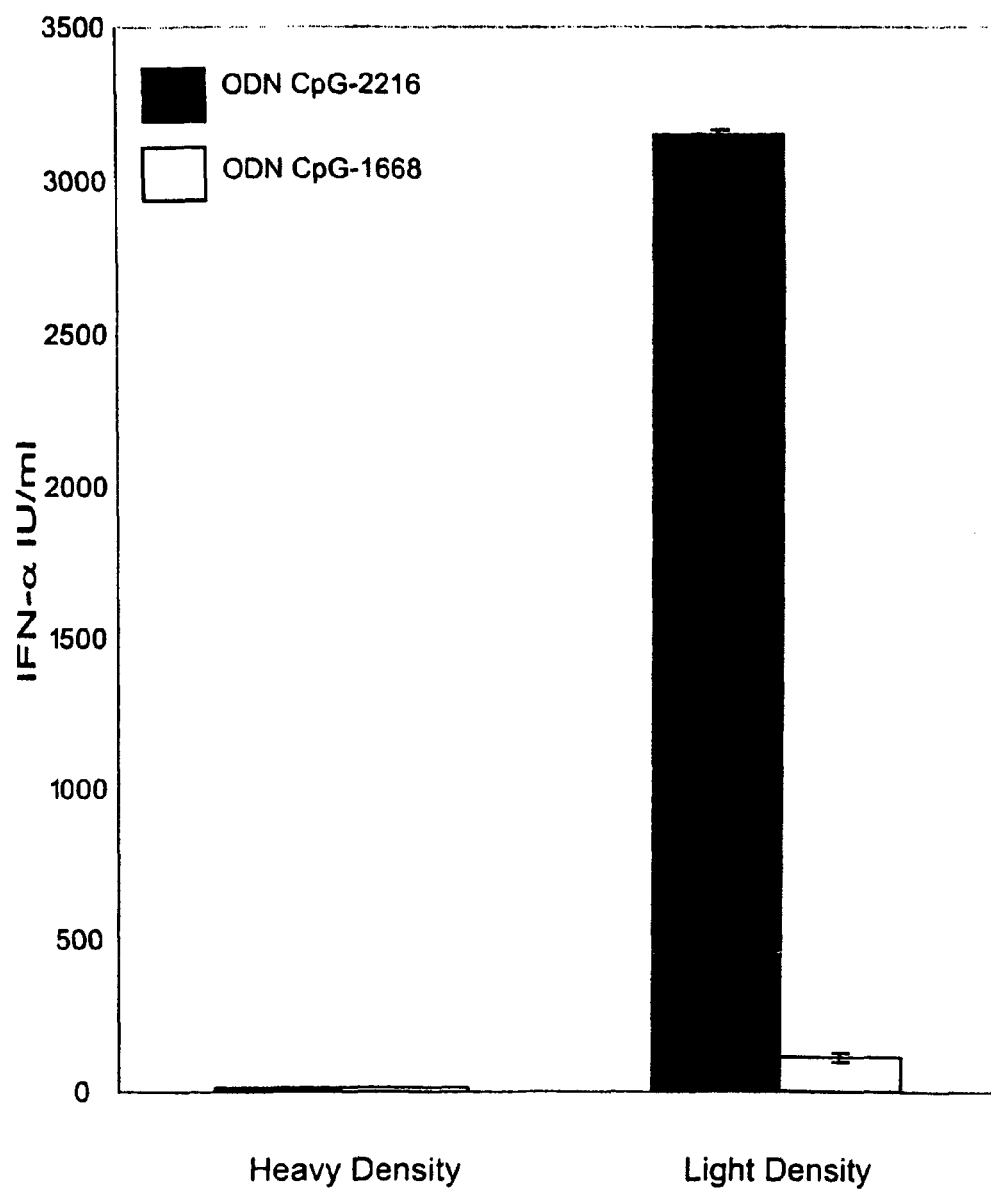
FIG. 1 depicts that the IFN-α produced in response to CpG-ODN in the BM comes from light density cells. BM cells were separated over a 10 ml 1.077 g/cm$^3$ Nycodenz® gradient and the 'light' cells (within the top 6 mls) and 'heavy' cells (bottom 4 mls) collected. The cells were stimulated with the A-type ODN CpG-2216 (black bars) or the B-type ODN CpG-1668 (clear bars) and the supernatants tested for IFN-α production. Data is 1 experiment representative of two separate experiments; error bars represent the SD between duplicate samples.

The present invention is further illustrated by the following Examples, which in no way should be construed as further limiting. The entire contents of all of the references cited throughout this application are hereby expressly incorporated by reference.

EXAMPLES

1. Mice

Female C57BL/6J mice were purchased from Harlan Winkelmann GmbH, Borchen, Germany and used at 6-10 wk of age. T cells used in allostimulatory mixed leukocyte reactions (allo-MLR) were from Balb/c mice and also purchased from Harlan Winkelmann GmbH. Mice expressing green fluorescent protein (GFP) under the ubiquitin promoter [C57BL/6-Tg(UBC-GFP)30Scha/J, referred to hereafter as UBC-GFP mice] were purchased from Charles River Laboratories (Sulzfeld, Germany) and bred in house. C57BL/6-Tg (TcraTcrb)1100Mjb/j (OTI) mice and mice harbouring a disrupted NFkb1 gene (B6;129P-Nfkb1$^{tm1Bal}$/J) were originally purchased from Jackson Laboratories and bred in house. FLKO mice were described by McKenna et al. 2000 and bred at the Institute of Labortierkunde (University of Zurich). Mice expressing a human Bcl-2 transgene expressed under the vav promoter have been described previously (Ogilvy et al. 1999) and were obtained from G. Hacker, Institute for Medical Microbiology, Immunology and Hygiene, Technical University of Munich.

Animal experiments were carried out with approval and under the guidelines of the local government animal ethics authorities.

2. Antibodies And Reagents

Recombinant (rec) flag-tagged murine (mu) FL was expressed in CHO cells and purified as previously described (O'Keeffe et al. 2002b). recmuGM-CSF and recmuM-CSF were from Tebu-Bio (Frankfurt, Germany). Oligonucleotides containing CpG motifs (CpG2216 and CpG1668) were synthesized by TIB MOLBIOL (Berlin, Germany) according to published sequences (Spies et al. 2003). Imiquimod (R837) and palmitoyl-3-cysteine-serine-lysine-4 (Pam-3-Cys) were purchased from InvivoGen (San Diego, USA). Poly(cytidylic-inosinic) acid (poly I:C) and lipopolysaccharide (LPS) were purchased from Sigma-Aldrich (Taufkirchen, Germany).

The MVA used for this study was MVA-BN®, developed by Bavarian Nordic and deposited at European Collection of Cell Cultures (ECACC) (V00083008) and MVA expressing ovalbumin. MVA was propagated and titered on primary chicken embryo fibroblasts (CEF) that were prepared from 11-day-old embryonated pathogen-free hen eggs (Charles River, Mass., USA) and cultured in RPMI-1640 medium supplemented with 10% FCS. ECTV strain Moscow was obtained from the American Type Culture Collection (ATCC) as VR-1372 and propagated and titered on Vero C1008 cells (ECACC 85020206). SFV was obtained from ATCC (VR-364) and propagated and titered on the rabbit cornea cell line SIRC obtained from ATCC (CCL-60). All cell lines were maintained in Dulbecco's Modified Eagle's Medium (DMEM; Invitrogen, Karlsruhe, Germany) supplemented with 10% FCS without antibiotics.

Antibodies were obtained from Becton Dickinson GmbH, Heidelberg, Germany, with the following exceptions: purified and FITC-conjugated anti-CD11c (rat clone 223H7) and anti-Ly49Q (Biozol Diagnostica Vertrieb GmbH, Eching, Germany), anti-mPDCA-1 (Miltenyi Biotec, Bergisch Gladbach, Germany) and anti-F4/80 (NatuTec GmbH, Frankfurt, Germany). Hybridomas, the supernatants of which were used in the depletion cocktail for ex vivo DC purification and also for BM DC purification, were kindly provided by Professor Ken Shortman, WEHI, Melbourne, Australia.

3. Isolation Of Cells From Bone Marrow And DC Purification

Femur and tibiae from mice were removed and cells were flushed from the bones with a 20 ml syringe filled with RPMI-1640 (Gibco/BRL, adjusted to mouse osmolarity) containing 2% FCS and fitted with a 21 g needle. Cells were resuspended by repeatedly flushing through the syringe. For preparation of light density cells the cells were pelleted by centrifugation and resuspended in Nycodenz® 1.077A (Progen Biotechnik, Heidelberg, Germany, adjusted to mouse osmolarity 308 mOsm). Density separation, incubation with antibody depletion cocktail and magnetic bead depletion were essentially as previously described (O'Keeffe et al. 2002a) except that anti CD49b mAb was also added to the depletion cocktail and anti-Thy1.1 was omitted. Hybridomas, the supernatants of which were used in the depletion cocktail, were kindly provided by Prof Ken Shortman, WEHI, Australia. For sorting of BM miDC and pDC, after depletion steps the cells were routinely stained with CD11c (PE-Cy7 or FITC), CD45RA-PE and CD11b (APC or Pacific Blue). On occasions, CD24-FITC was also included in the stain. Cells were sorted as pDC ($CD11c^{int}CD45RA^{hi}CD11b^-$) or miDC ($CD11c^{int}CD45RA^-CD11b^-HSA^{int}$).

Splenic DC were isolated as previously described (O'Keeffe et al. 2002a) using the Nycodenz® and depletion cocktail described above.

4. Stimulants Of DC

Oligonucleotides containing CpG motifs (CpG2216 and CpG1668) were synthesized by TIB MOLBIOL (Berlin, Germany) according to published sequences. Spies B, et al. (2003) *Journal of Immunology* 171(11):5908-5912. Imiquimod (R837) and palmitoyl-3-cysteine-serine-lysine-4 (Pam-3-Cys) were purchased from InvivoGen (San Diego, USA). Resiquimod (R848) was purchased from Alexis Biochemicals (Axxora Deutschland GmbH, Lorrach, Germany). Poly (cytidylic-inosinic) acid (poly I:C) and lipopolysaccharide (LPS) were purchased from Sigma-Aldrich (Taufkirchen, Germany).

Recombinant flag-tagged murine FL was expressed in CHO cells and purified as previously described (O'Keeffe et al. 2002b). Recombinant murine GM-CSF and M-CSF were purchased from Tebu-Bio (Frankfurt, Germany).

The MVA used for this study was MVA-BN®, developed by Bavarian Nordic and deposited at European Collection of Cell Cultures (ECACC) (V00083008). MVA was propagated and titered on primary chicken embryo fibroblasts (CEF) that were prepared from 11-day-old embryonated pathogen-free hen eggs (Charles River, Mass., USA) and cultured in RPMI-1640 medium supplemented with 10% FCS. Ectromelia Virus (ECTV) strain Moscow was obtained from the American Type Culture Collection (ATCC) as VR-1372 and was propagated and titered on Vero C1008 cells (ECACC 85020206). Shope Fibroma Virus (SFV) was obtained from ATCC (VR-364) and propagated and titered on the rabbit cornea cell line SIRC obtained from ATCC (CCL-60). All cell lines were maintained in Dulbecco's Modified Eagle's Medium (DMEM; Invitrogen, Karlsruhe, Germany) supplemented with 10% FCS without antibiotics.

5. DC Stimulation And Cytokine Quantitation

Stimulation of dendritic cells was carried out at 0.25-0.5× $1.0 \times 10^6$ cells per ml in round bottom plates or v-bottom plates for volumes of 50 µl or less. Cells were stimulated for 18-48 hrs in complete media (RPMI-1640 media supplemented with 10% FCS, 500 beta-mercaptoethanol, 100 IU/ml penicillin/streptomycin) with or without added stimulus. The stimuli used were as follows; 10 ng/ml GM-CSF, 1 µg/ml Pam-3-Cys, 100 µg/ml poly(I:C), 1 µg/ml LPS, 1 µg/ml R837, 0.5 µM CpG2216, or 0.5 µM CpG1668.

Culture supernatants were assayed for IFN-α and RANTES by two-site ELISA as previously described (O'Keeffe et al. 2002a). United States Biological Mab clone 8.S.415 (THP Medical Products Vertriebs GmbH, Vienna, Austria) was used as capture Mab for the IFN-beta ELISA and PBL InterferonSource detection abs (rabbit anti-mouse IFN-beta) and mouse IFN-beta standard were purchased from Tebu-Bio. Other cytokines (IL-12 p70, IL-6, IL-10, TNF-α MCP-1 and MIP-3alpha) were measured using the Cytometric Bead Array, Mouse Inflammation Kit (Becton Dickinson).

6. CFSE Labelling

T cells or miDC were labelled with a final concentration of 2 µM CFSE using the CellTrace CFSE Cell Proliferation Kit, Molecular Probes (Invitrogen GmbH, Karlsruhe, Germany), according to the manufacturer's instructions.

7. Allogeneic MLR

DC subsets were purified from BM and spleen and sorted to greater than 95% purity using a FACS-ARIA. T cells from Balb/c mice were purified from subcutaneous and mesenteric lymph nodes. Purified T cells were labelled with 2 µM CFSE using the CellTrace CFSE Cell Proliferation Kit (Molecular Probes, Invitrogen GmbH, Karlsruhe, Germany). Triplicates of fifty thousand T cells were incubated with DC subsets in media or with the addition of stimuli including GM-CSF, LPS or CpG2216. After 4 days at 37° C. the replicate samples were analysed by FACS to ascertain the degree of T cell division (loss of CFSE fluorescence). An aliquot of beads used for quantitation were also added to each well so that absolute numbers of divided T cells could be enumerated.

8. OTI T Cell Stimulation

A cross-presentation assay was similarly carried out to the MLR above, whereby T cells from OTI transgenic mice were utilized instead of Balb/c T cells and DC were first incubated with ovalbumin for 1 hr at 37° C., washed and then added to the T cells. The ability of DC subsets to present ovalbumin presented by MVA was analysed by first incubating the DC with MVA-Ova for 1 hr at 37° C., followed by washing in complete media. CFSE-labelled T cell replicates were then incubated with $10^3$, $3 \times 10^3$, or $10^4$ infected DC. As controls, DC were also included that were incubated with MVA (not expressing OVA) or untreated. T cell controls included were T cells alone and T cells that were incubated with MVA-OVA as for the DC subpopulations, without any addition of DC. After 4 days of incubation, cells from pooled replicate samples were analysed for CFSE expression and quantitation beads were included in each sample to enumerate cell numbers.

9. Transfer Of UBC-GFP DC Into C57BL/6 Mice

BM pDC and miDC were purified and sorted from UBC-GFP mice, washed in MTPBS, and injected into the tail vein of C57BL/6 mice. Three mice per cell group were injected with either 0.6×10⁶ pDC or 0.3×10⁶ miDC in 100 µl MTPBS per mouse. Three mice received MTPBS only. Approximately 90 hr after transfer, the recipient mice were euthanized and bm and spleen DC prepared, keeping each mouse that received cells separate. Donor cells were selected by gating on GFP (FITC)$^{hi}$ and PI$^{neg}$ cells.

10. BM Non-pDC IFN-α Producing Cells Are CD11c$^{lo}$CD11b$^{-/lo}$ Cells That Do Not Express B, T Or NK-Specific Markers It has been previously shown that conditions resulting in pDC removal in BM do not remove all IFN-α production in response to CpG-ODN stimulation (Hochrein et al. 2004). Liu and colleagues have previously published that human early pre-pDC that do not yet have the complete pDC phenotype, also have the ability to produce high levels of IFN-I (Blom et al. 2000). It was found that no other organ apart from BM retained any IFN-α producing capacity to CpG-ODN if pDC were first removed, and it was considered that pDC precursors might be the cells that remained after CD45R/CD45RA depletion of mouse BM cells.

Light density separation of BM cells revealed that all of the IFN-α activity in response to CpG-ODN segregated with the light density fraction of BM cells (FIG. 1).

Figure 2A:
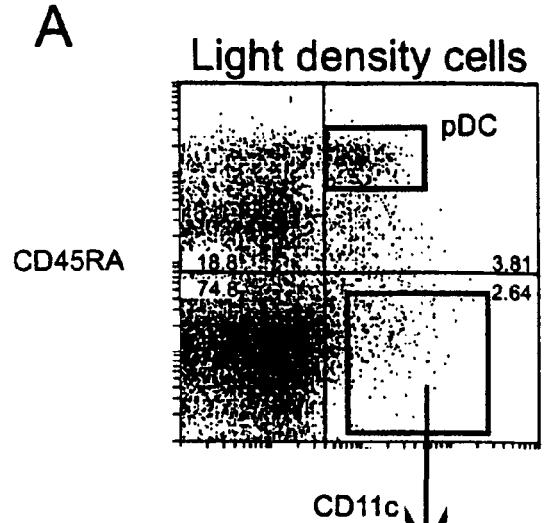
FIGS. 2A-F depict that non-pDC, CD11c$^+$CD45RA$^-$ BM cells also produce high levels of IFN-α in response to CpG-2216. A. Light density cells were stained with CD45RA and CD11c. B. The surface phenotype of boxed cells in A depleted of CD3$^+$, CD19$^+$, CD49b$^+$ cells (black filled line) is compared to that of pDC (black unfilled line). Unstained cells are dotted black line. C. Non-pDC cells in B co-stained with CD24 and CD11b. All of the IFN-α production was located in the CD24$^{int}$CD11b$^-$ cells shown boxed. Their IFN-α production in response to CpG2216 is shown (black bar) and compared to BM pDC (clear bar). D. Light density cells in B gated on CD11b$^-$ cells showing the phenotype of the IFN-α producing cells with respect to CD11c and CD24. E. The morphology of the pDC (upper box in D) and IFN-α producing CD45RA$^-$ cells boxed in D are compared after overnight incubation in media alone, GM-CSF or CpG-2216. F. The phenotype of IFN-α producing CD45RA$^-$ cells boxed in D is shown as black filled line. Black dotted line indicates unstained background control. Black line indicates pDC. A, F are representative of two experiments. B is representative of three experiments. C, D, E are representative of more than ten experiments.
Figure 2B:
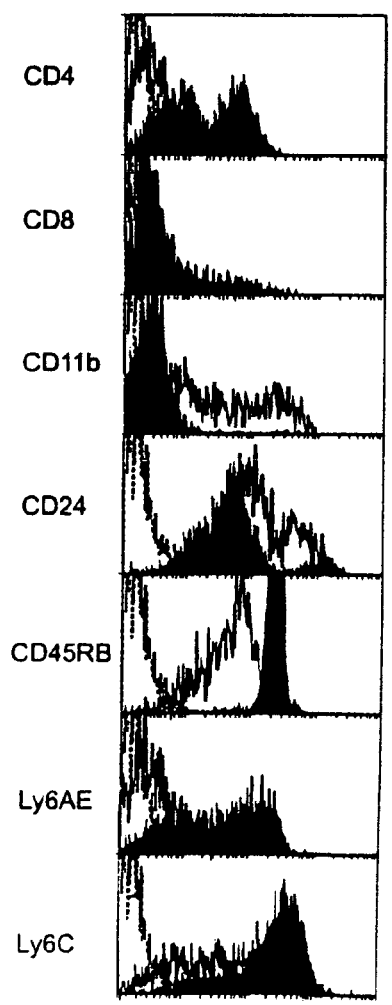
Figure 2C:
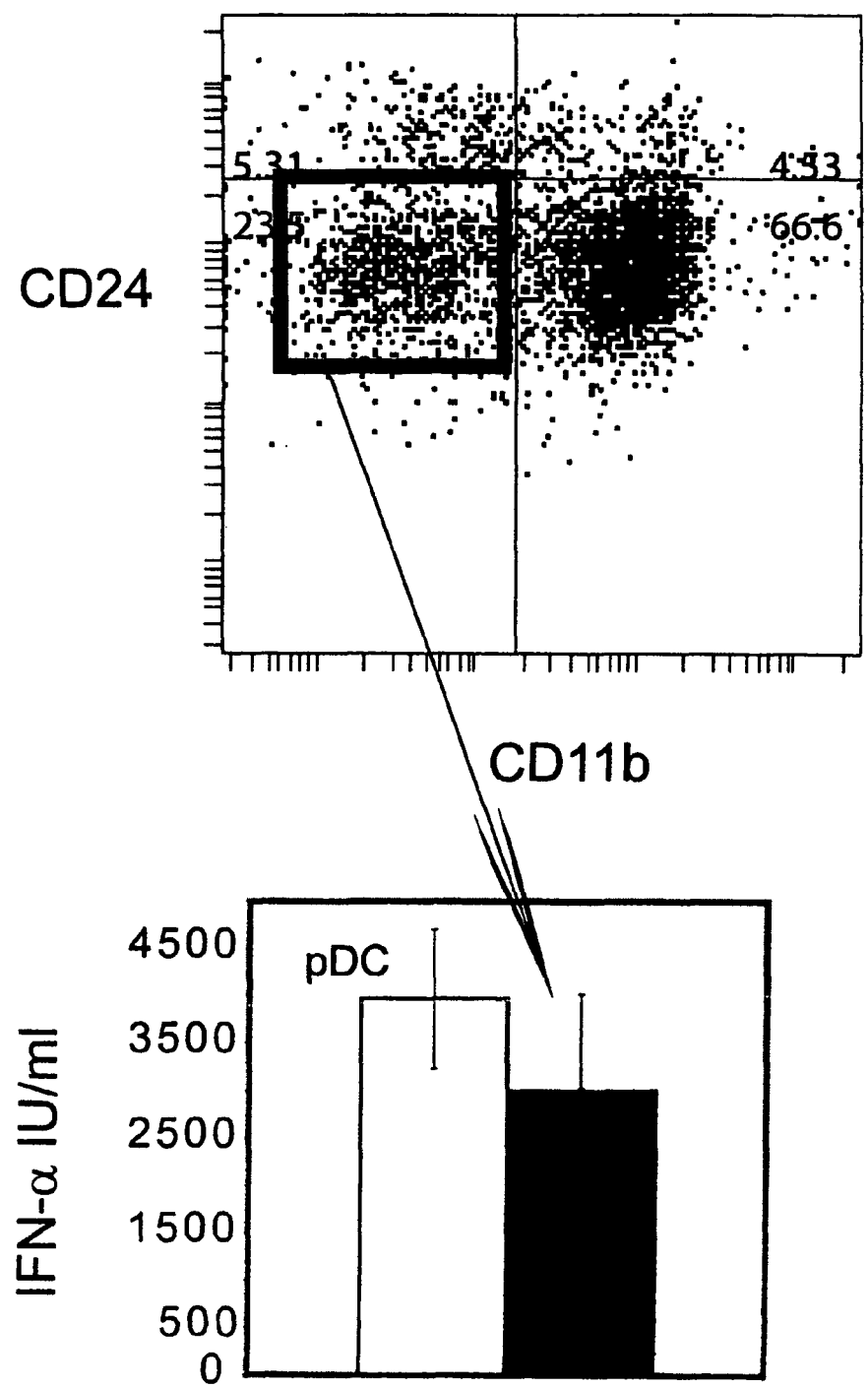
Figure 2D:
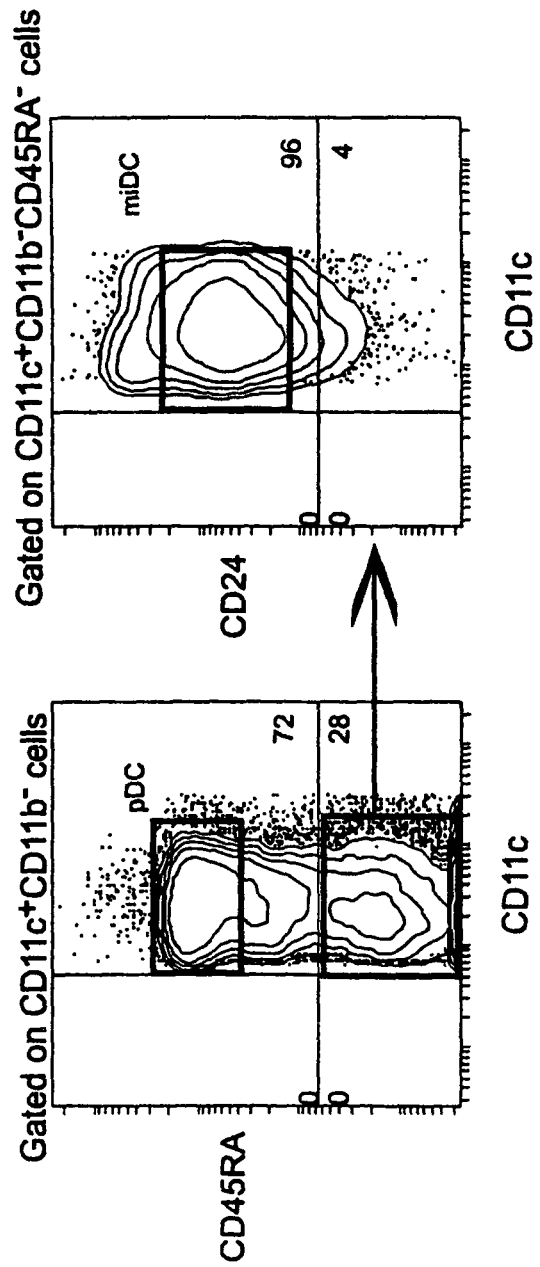

Light density BM cells were then purified and stained with CD45RA and CD11c (FIG. 2A). Three crude cell populations were sorted: pDC, CD11c⁺ putative BM cDC, and 'the rest'. Each of these three populations was stimulated with CpG-2216 overnight and the supernatants tested for IFN-α activity. Apart from pDC, the CD11c+CD45RA⁻ cell population also produced IFN-α. The CD11c⁺ cell population was heterogeneous, containing small numbers of cells expressing CD3, CD19, CD49b and NK1.1. The cell sorting was repeated including antibodies to these surface markers in a junk channel. The CD11c+CD3⁻CD19⁻CD49b⁻Ly6G⁻NK1.1⁻ cells retained their high expression levels of IFN-α in response to CpG-2216. The remaining CD11c+ cells, including CD49b⁺ CD11c⁺ cells, did not produce IFN-α in response to CpG-2216. Extensive surface phenotyping of the CD11c⁺ CD45RA⁻ BM cells that were depleted of CD3⁺, CD19⁺, and CD49b⁺ cells was carried out (FIG. 2B). It was found that the cells were heterogeneous for CD11b and CD24 expression, with 40-50% of the cells expressing medium to high levels of CD11b and the remaining were CD11b$^{-/lo}$ (FIG. 2). A small population of Ly6G⁺ cells was present, removal of these with Gr-1-specific abs did not affect IFN-α production and so anti-Gr-1 abs were routinely included in the purification. The cells could be sorted to discrete populations by staining the CD3⁻ CD19⁻CD49b⁻Ly6G⁻NK1.1⁻ BM cells with CD11c, CD45RA, CD24, and CD11b (FIG. 2C). Of the CD45RA⁻ cells, the IFN-α capacity segregated precisely with the CD24$^{int}$CD11b⁻ cells and the amount produced was similar to that produced by BMpDC (FIG. 2D).

As shown in FIG. 2, the CD11b$^{-/lo}$CD24$^{int}$ cells lacked expression of CD4 or CD8α. They expressed intermediate levels of CD24, high levels of Flt3, high levels of CD172 (Sirpα), low levels of co-stimulation markers CD40 and CD80, intermediate levels of CD86, and low levels of MHCII. They did not express Clec9a. Thus, by phenotypic comparison, the non-pDC IFN-α producing cells of BM differed from Lin-MDP or CDP precursors (Liu et al. 2007), and from the spleen CD3⁻ CD19⁻ NK1.1⁻ Ter119⁻ CD45RA$^{neg-lo}$CD11c+ CD43+SIRP-α$^{lo}$ pre-cDC (Naik et al. 2006), or the CD11b⁺ BM pre-DC (Naik et al. 2007), or spleen or BM CD11c–pro-DC.

Figure 2E:
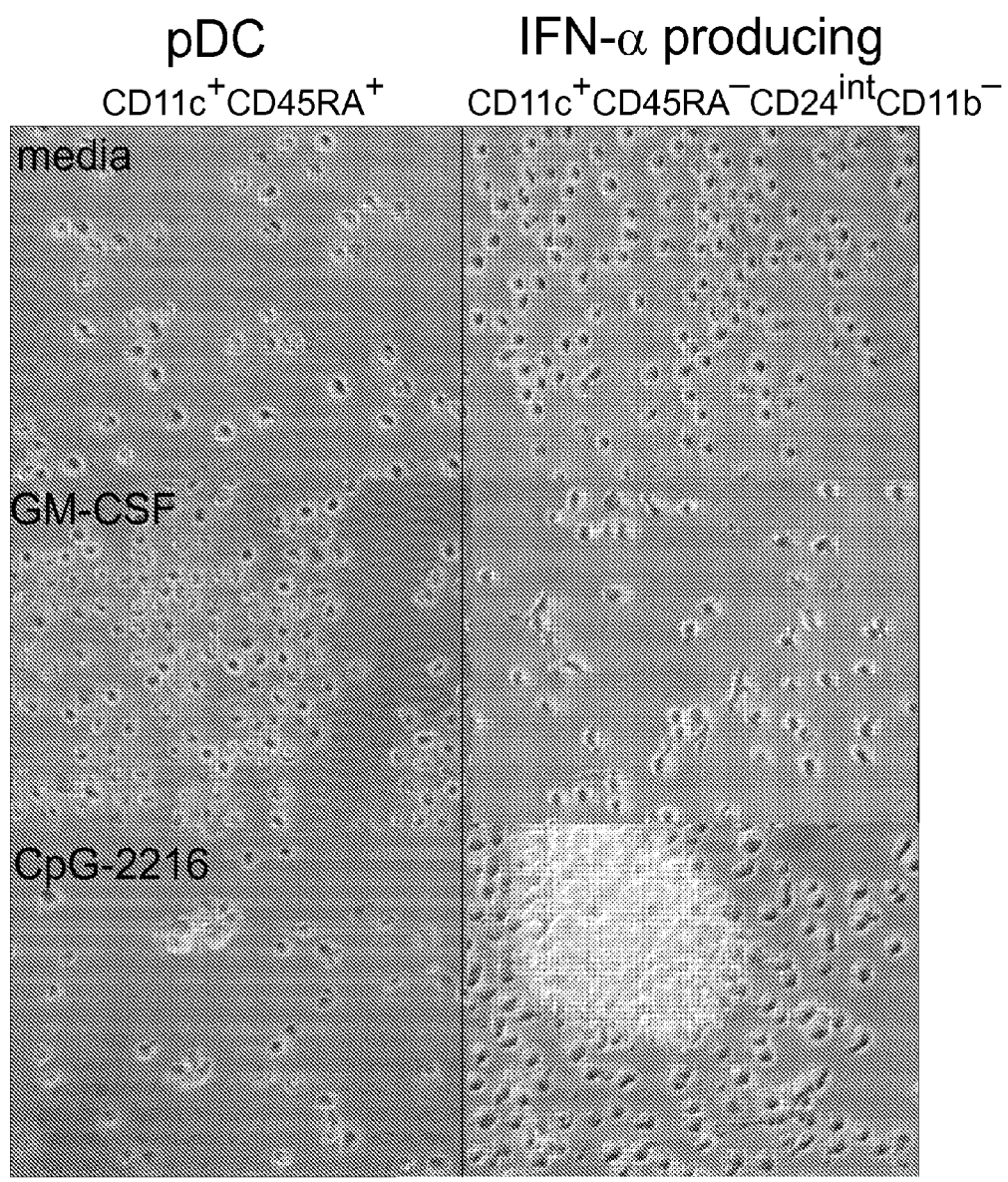
Figure 2F:
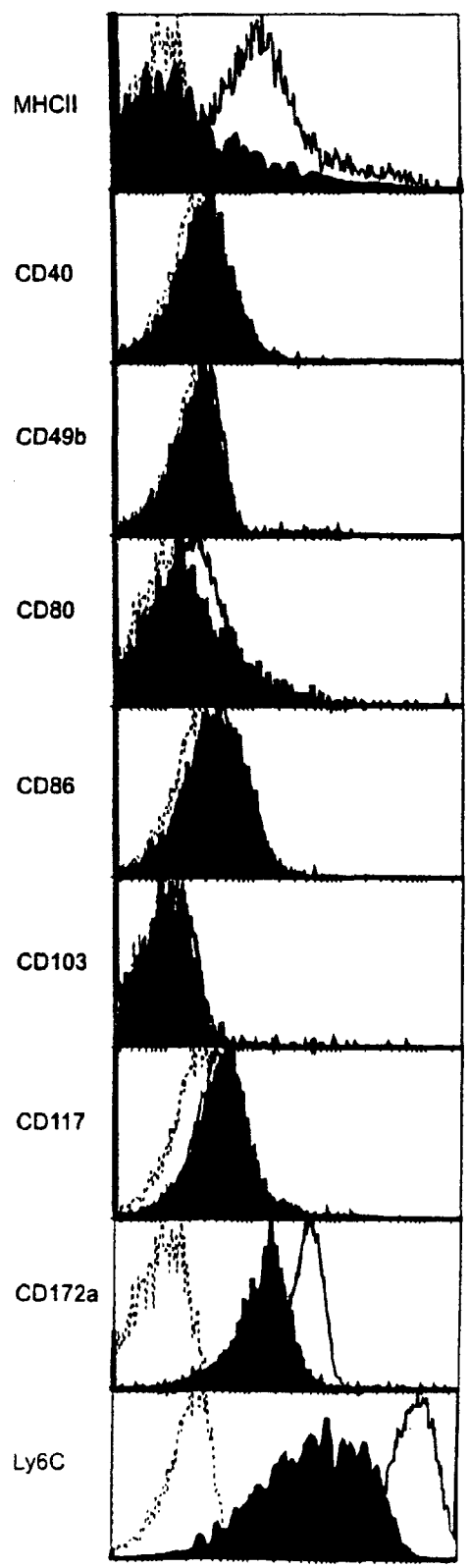

11. Activation Of BM Non-pDC IFN-α Producing Cells Induces DC-Like Transformation But miDC Respond To TLR Ligands And Growth Factors Differently to pDC The CD11c+CD45RA⁻CD24$^{int}$CD11b⁻ cells or BMpDC were stimulated overnight with CpG2216, GM-CSF, or media and their morphology compared. In media, the CD11c+CD45RA⁻CD24$^{int}$CD11b⁻ cells and pDC behaved similarly, with no sign of typical DC morphology in either population. However, surprisingly, the CD11c+CD45RA⁻ CD24$^{int}$CD11b⁻ cells, unlike the pDC, were clearly matured in GM-CSF (FIG. 2E). Moreover, they responded extremely well to CpG-2216, forming large clusters of cells with typical cytoplasmic processes, unlike the small clusters of cells formed in the pDC cultures.

The CD11c+CD3⁻CD19⁻CD49b⁻Ly6G⁻NK1.1⁻ CD24$^{int}$CD11b$^{-/lo}$ cells were potent producers of IFN-α to CpG-2216 and they appeared activated in GM-CSF. Their cytokine response to a range of TLR ligands and GM-CSF was tested. As shown in FIG. 3A, the cells produced high levels of IFN-α to CpG-2216 and reproducibly low levels to a TLR7 ligand R837. They also produced low levels of IFN-α to MVA virus. The IFN-α production was only detected amongst the CD11c+CD3⁺CD19⁻CD49b⁻Ly6G⁻NK1.1⁻ CD24$^{int}$CD11b$^{-/lo}$ cells, with no production detectable by the CD11b⁺ cells.

The CD11c⁺CD3⁻CD19⁻CD49b⁻Ly6G⁻NK1.1⁻ CD24$^{int}$CD11b$^{-/lo}$ cells produced IL-6 and TNF-α in response to TLR9 and 7 ligands and lower, although reproducible, levels of IL-6 in response to TLR2 (Pam3Cys) and TLR4 ligands (LPS) (FIG. 3B). The IL-6 response to CpG-2216 was particularly high. In the same conditions using CpG-A-ODN, IL-6 is barely detectable from BM pDC. IL-10 and MIP-3α were also measured, and were not detected in any conditions. Very low levels of IL-12p70 (<100 pg/ml) were produced in some experiments in response to CpG-2216 but only if GM-CSF was additionally included in the medium. None of the cytokines was produced in response to GM-CSF alone. The response of the cells to M-CSF and Flt3-Ligand was also tested, and none of the tested cytokines were produced, nor were any morphological changes noted.

Their activated surface phenotype resembled in some ways the phenotype of pDC, showing upregulation of CD8α, CD40, CD86, and CD11c in response to CpG-2216 (FIG. 4A). However, the expression of MHCII and co-stimulation markers including CD40, CD80, and CD86 was at least 5-10 fold higher on the activated CD49b⁻Ly6G⁻NK1.1⁻ CD24$^{int}$CD11b$^{-/lo}$ cells in all conditions tested.

The expression of CD45R was upregulated on the CD49b⁻ Ly6G⁻ NK1.1⁻CD24$^{int}$CD11b$^{-/lo}$ cells in all conditions (FIG. 4B), never as high as on pDC, but nevertheless the expression of CD45R did suggest a relationship to the pDC. However, TLR2 and 4 ligands also induced upregulation of co-stimulation markers (FIG. 4C), but had no effect on pDC. Moreover, unlike pDC, low levels of co-stimulation markers were observed after overnight incubation in media alone which was further enhanced by GM-CSF (FIGS. 4A and 4C).

These observations, together with the differential functions described below, led to naming the CD11c+CD3⁻CD19⁻

CD49b$^-$Ly6G$^-$NK1.1$^-$CD11b$^{-/lo}$ cells as a novel BM DC population, myelos (bone marrow in Greek) interferon DC (or miDC).

12. miDC Are Infected By Virus But Survive Well And Respond Differently To Various Viruses Than pDC The response of miDC to CpG2216, including IFN-α production and surface activation, resembled the pDC, suggesting that they were possibly a differentiation state or different subset of pDC. However, the response of miDC to LPS and to GM-CSF suggested that the miDC were fundamentally different from pDC. The activation of miDC with various viruses shed further light on the differences between these two cell types. HSV, known to activate BM pDC via TLR9 and TLR9-independent pathways, was also a strong inducer of miDC surface activation and IFN-α production (FIG. 5). miDC produced substantial levels of IFN-α in response to HSV, although this was still about 50% of that produced by pDC. HSV, like CpG-2216, also induced high IL-6 production from miDC, more than 10-fold that produced by pDC and also more than double that produced by spleen cDC. MVA induced CD86 upregulation on miDC and low levels of IFN-α production, about one third that produced by pDC. It should be noted that no IFN-α was detected in supernatants from spleen cDC.

Figure 5A:
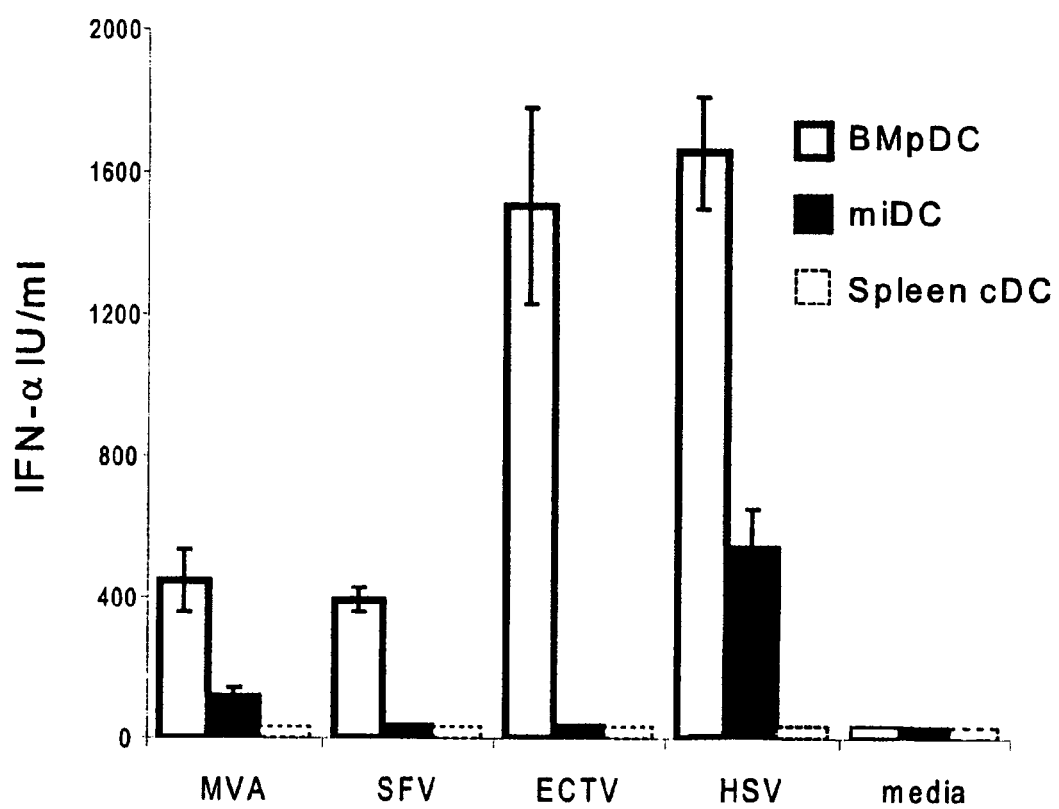
FIG. 5A-C depict viral activation of miDC. A. BMpDC, miDC or spleen cDC were purified by FACS sorting and stimulated for 20 h with the viruses as shown and supernatants were tested for IFN-α production by ELISA. Data are from one experiment representative of at least 2 experiments for each virus. Error bars represent SD of duplicate samples. B. Staining of CD86 and CD45R on miDC (black unfilled line) or pDC (dotted black line) stimulated as shown. Filled black line represents staining of miDC after 20 h in media only. C. The survival of pDC or miDC after 20 h culture is shown. Data are from one experiment representative of at least three experiments.
Figure 5B:
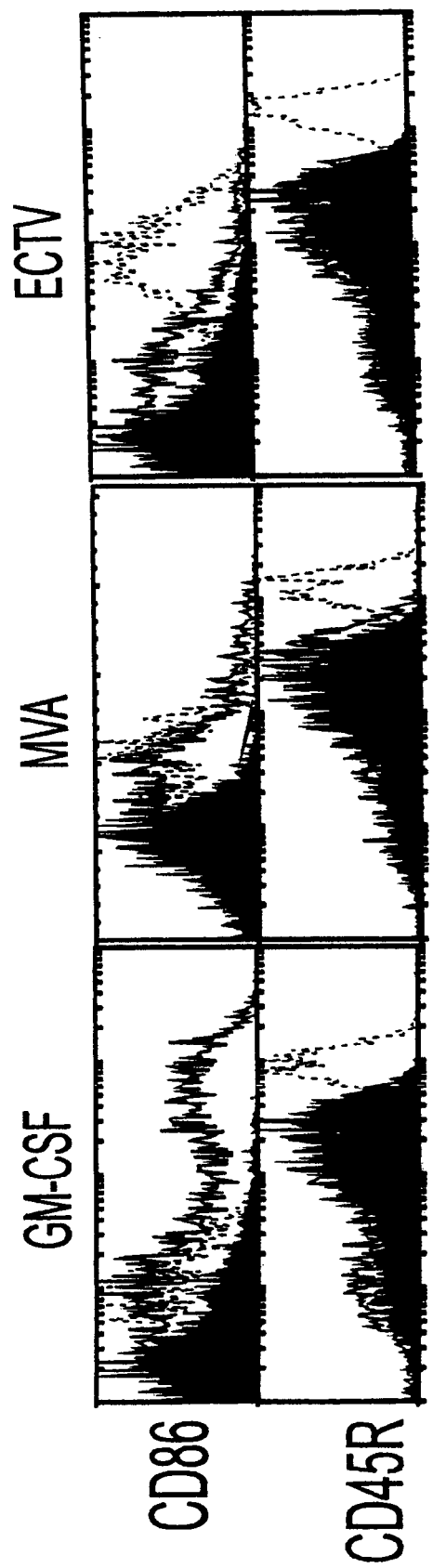
Figure 5C:
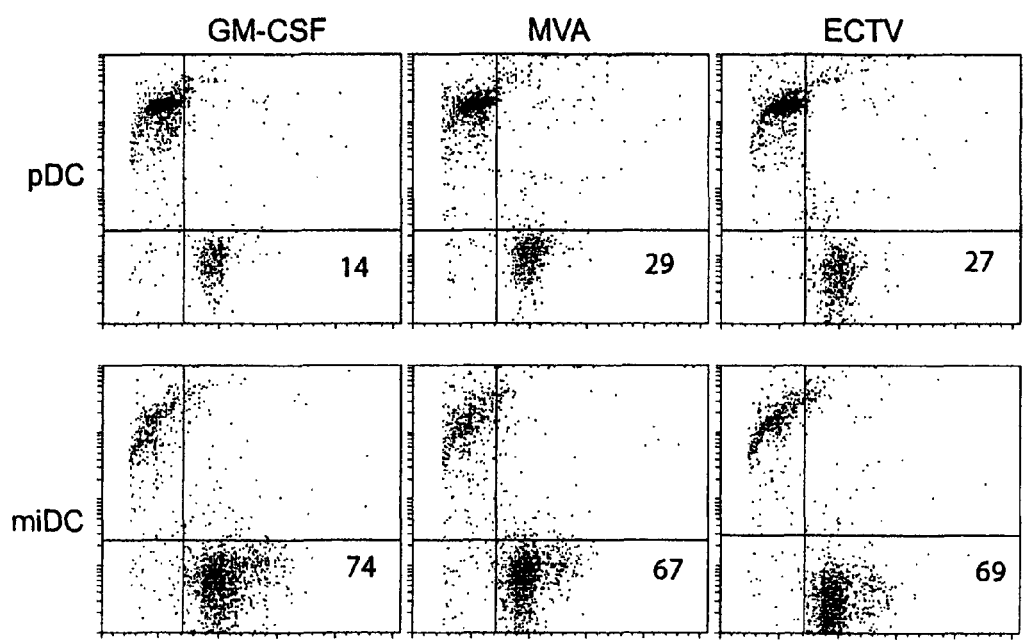

Ectromelia and Shope Fibroma viruses are both members of the pox virus family, that have previously been shown to activate pDC via TLR9, but to potently inhibit the largely TLR9-independent activation pathways of cDC. Both of these viruses, Shope fibroma (SFV) and Ectromelia (ECTV) induced no surface activation of miDC, nor measurable IFN-α or IL-6 or TNF-α production (FIG. 5). Thus, miDC responded to these pox viruses similarly as cDC, exhibiting no activation in response to these pathogenic pox viruses.

A general feature of the response of miDC to all of the viruses and other stimuli tested was that they displayed high survival (more than 65%, FIG. 5), whether activated or not, differentiating these cells from the pDC that exhibit poor survival upon stimulation with all of these viruses.

Figure 9:
FIG. 9 depicts cytokine response of the indicated DC from Bcl2 transgenic or non-transgenic mice to the indicated stimuli.

It has been previously found that pDC from Bcl2-transgenic mice survive extremely well upon culture and activation (O'Keeffe et al. 2005). It was found that the miDC purified from Bcl2-transgenic mice did not have a survival advantage over that of C57BL/6 mice. In fact, the survival of C57BL/6 miDC paralleled that of the pDC from the Bcl2 transgenics. It was found that miDC from Bcl2 transgenic mice also did not produce cytokines in response to SFV or ECTV (FIG. 9), although the pDC displayed increased IFN-α production to these viruses.

13. Qualitative Differences Between miDC And pDC

Figure 3:
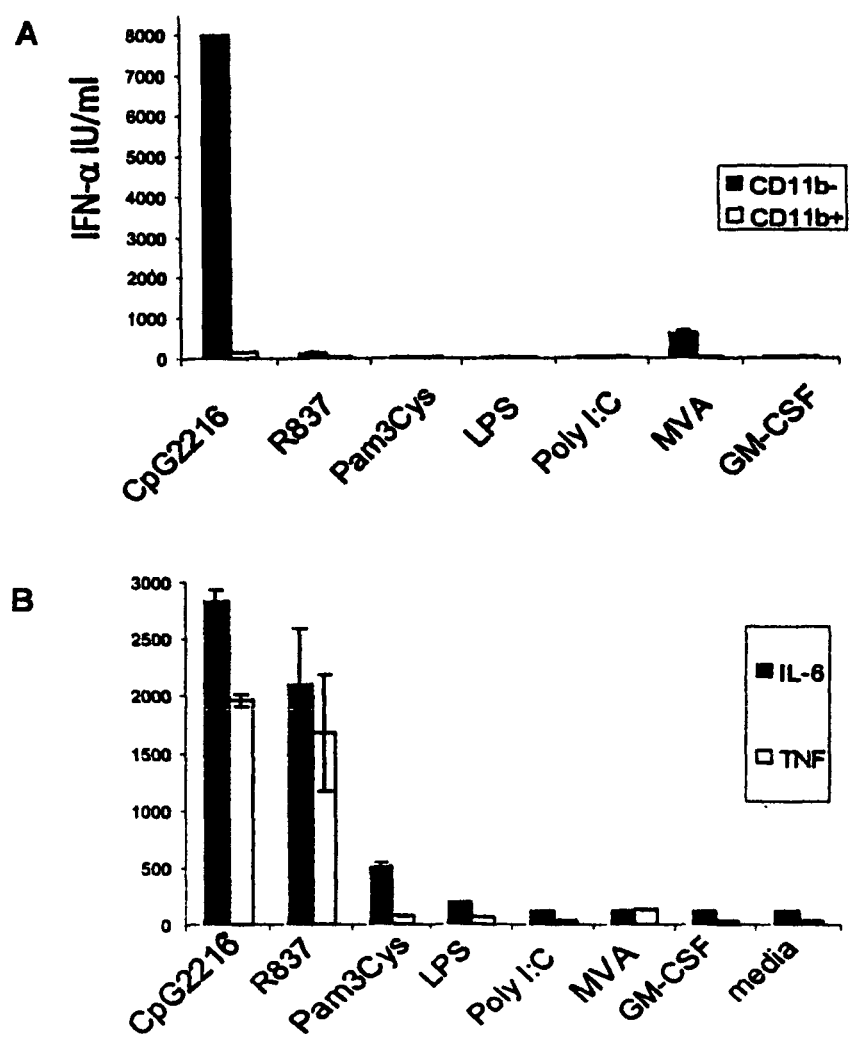
FIGS. 3A and B depict CD11c$^+$CD24$^{int}$CD11b$^-$ cells respond with cytokine production to multiple TLR ligands. A. The CD11c$^+$CD24$^{int}$CD11b$^-$ and CD11c+CD24$^{int}$CD11b$^+$ BM cells were sorted and stimulated with TLR ligands, MVA, or GM-CSF as shown. Supernatants were tested by ELISA for IFN-α production. Error bars represent SD of duplicate samples. Data for CD11b$^-$ cells is representative of more than 5 experiments. Data for CD11b$^+$ cells is representative of two experiments. B. IL-6 and TNF production was measured with the indicated stimuli.
Figure 4:
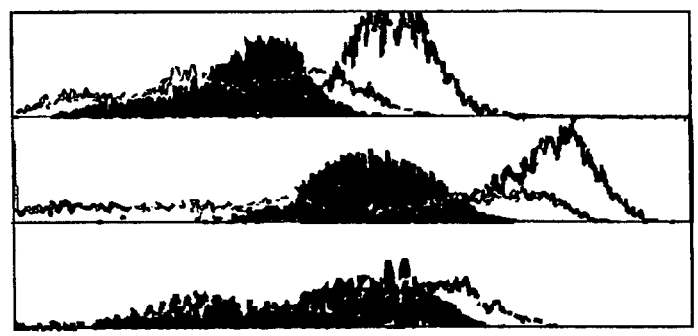
FIG. 4A-C depict that CD11c$^+$CD24$^{int}$CD11b$^-$ cells respond with surface activation to multiple TLR ligands and upregulate CD45R on their surface. pDC or CD11c$^+$ CD24$^{int}$CD11b$^-$ cells were purified by FACS sorting from pooled BM of at least 20 mice. A. Cells were stimulated with CpG-2216 for 18 h and then stained with the surface markers shown. Dotted black line is miDC in GM-CSF, filled histogram is staining of pDC in CpG-2216, black line is staining of CD11c$^+$CD24$^{int}$CD11b$^-$ cells in CpG-2216. Unstained control for CD11c$^+$CD24$^{int}$CD11b$^-$ cells and pDC was in first log for all markers but not shown for clarity. Data are from one experiment representative of 3 experiments for CD40 staining and more than 5 experiments for CD8α and CD86 staining. B. The expression of CD45R (B220) is shown on pDC (filled black line), CD11c$^+$CD24$^{int}$CD11b$^-$ cells in GM-CSF (dotted black line) or in CpG2216 (black line). Data are representative of more than five experiments. C. CD86 expression (filled black line) is shown on CD11c$^+$ CD24$^{int}$CD11b$^-$ cells after 18 h incubation with the stimuli shown. Black dotted line is unstained background control. Data are from one experiment representative of more than ten experiments (CpG2216 and media) or at least three experiments for other stimuli.
Figure 4:
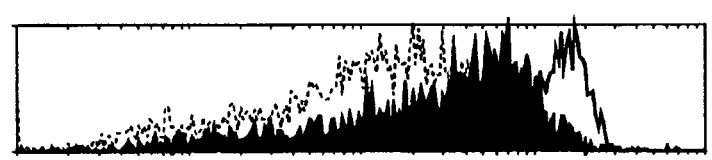
Figure 4:
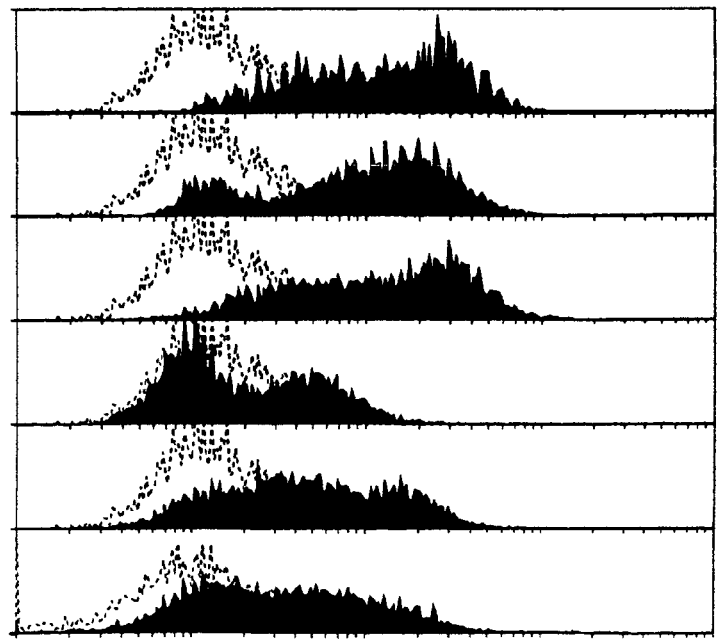

The miDC clearly displayed a far superior cell surface activation than the BM pDC in response to CpG-2216 (FIG. 4). Notably CpG2216-ODN induces barely detectable IL-6 production from pDC but in stark contrast, CpG2216-ODN induces high levels of IL-6 production from the miDC (FIG. 3). Moreover, miDC displayed a far superior survival to the pDC, resembling the survival of pDC from Bcl2 transgenic mice. To further test the relationship of the miDC to pDC, the TLR9 response of pDC and miDC purified from mice lacking the p50 subunit of NF-kB (nfkb1$^{-/-}$ mice) was tested. As previously shown for spleen pDC and pDC from FLDC cultures, the BM pDC of nfkb1$^{-/-}$ mice display substantially diminished IL-6 production (>80% reduction) upon activation with CpG1668-ODN. However, the miDC from nfkb1$^{-/-}$ mice showed only a mild (about 20%) reduction in IL-6 production capacity, similar to the response previously seen in spleen conventional DC of nfkb1$^{-/-}$ mice (O'Keeffe et al. 2005).

Figure 6:
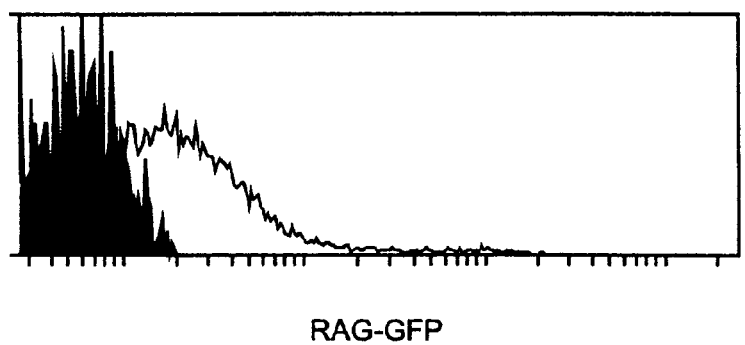
FIG. 6 depicts expression of Rag in miDC and pDC. DC were enriched from light density BM cells of Rag-GFP mice and pDC (unfilled black line) or miDC (filled black line) were gated and analysed for expression of GFP. Results are from one experiment of three pooled mice.

Pelayo et al. have shown that the BM pDC of mice expressing Rag-GFP are composed of 2 groups, GFP$^+$ (pDC1) and OFF (pDC2) cells that display differences in cytokine production (Pelayo et al. 2005). They demonstrated that pDC2 produced substantially more IFN-α than the pDC1 cells and in addition the pDC2 produced quite high levels of IL-6 and IFN-α in response to CpG-ODN. The GFP expression in miDC purified from these Rag-GFP mice was examined. It was found that miDC did not express GFP and thus lacked a Rag 'signature', clearly differentiating them from the pDC1 (FIG. 6). Moreover, although miDC produced substantial amounts of IL-6, resembling pDC2, they lacked IFN-α production to any TLR or viral stimulus tested and their surface activation upon stimulation was substantially stronger than that shown by Pelayo et al. for pDC1 or pDC2 (26). Thus, in addition to the stimulation and survival data, the lack of expression of Rag by miDC differentiates them from the pDC of BM.

14. miDC do not Divide Upon Activation

Figure 7A:
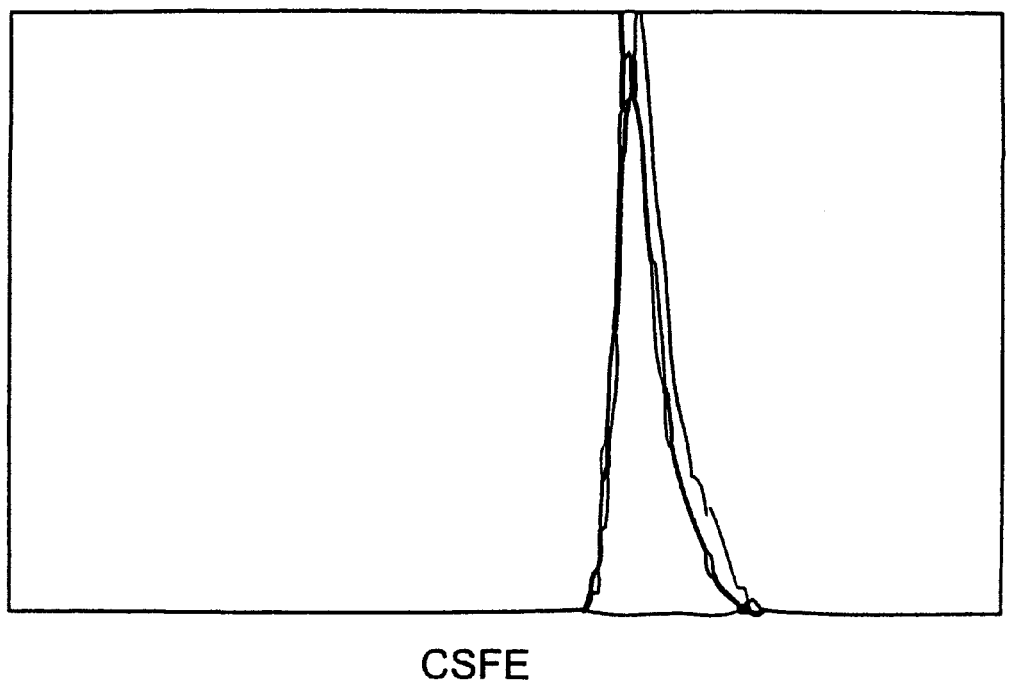
Figure 7C:
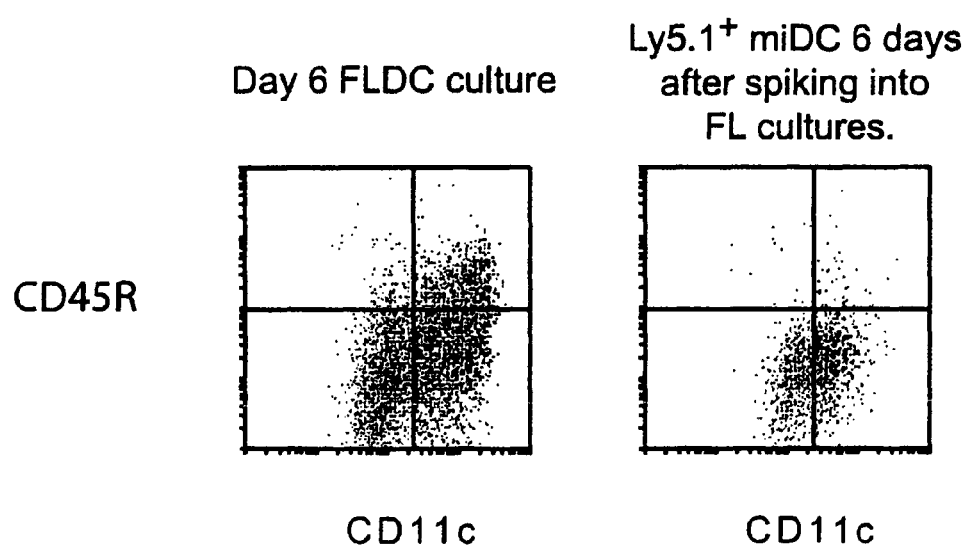

Upon activation, the miDC displayed features similar to pDC, including the expression of CD45R and the production of high levels of IFN-α upon CpG2216-ODN stimulation. Concomitantly, the miDC displayed features of cDC: maturation in response to GM-CSF, responsiveness to TLR4 ligands and high levels of IL-6 production in the absence of nfkb1. Moreover, the survival of the miDC, both in media and upon stimulation, was extremely high (FIG. 6). Given these factors, the possibility was considered that the miDC were in fact a dividing precursor population that gave rise to both pDC and cDC-like progeny. To test this hypothesis, the miDC were labelled with CFSE and cultured for 40 hrs in media alone or in the presence of ligands to TLR4, 7 or 9 or GM-CSF. FACS analysis of the miDC after the culture period revealed that there was no loss of CFSE label in any of the culture conditions, indicating that the miDC were non-dividing cells (FIG. 7A). CFSE-labelled and unlabelled miDC were compared for their ability to produce IFN-α, IL-6 and TNF-α after stimulation. The CFSE-labelled cells behaved exactly as their non-labelled counterparts.

15. miDC Divide 1-2 Times within FLBM Cultures

FLBM cultures drive cDC and pDC development from DC precursors with FL. In order to further investigate the proliferative capacity of the miDC they were labelled with CFSE and 'spiked' into FLBM cultures. After day 4 most of the miDC had undergone one division and by day 5 the cells were mainly cells that had divided either once or twice (FIG. 7B). In culture, the cells upregulated CD45R, but upon division CD45R was lost from the cell surface. The cells expressed high levels of Sirpα (CD172) and negligible Clec9A. Thus, they resembled more CD8$^-$ type FLDC.

16. miDC Display Potent Stimulation of Allogeneic and Antigen-Specific T Cells To determine the stimulatory capacity of miDC, they were first tested in an allogeneic MLR. Like pDC, they were poor stimulators of allogeneic T cells without prior activation.

Figure 8A:
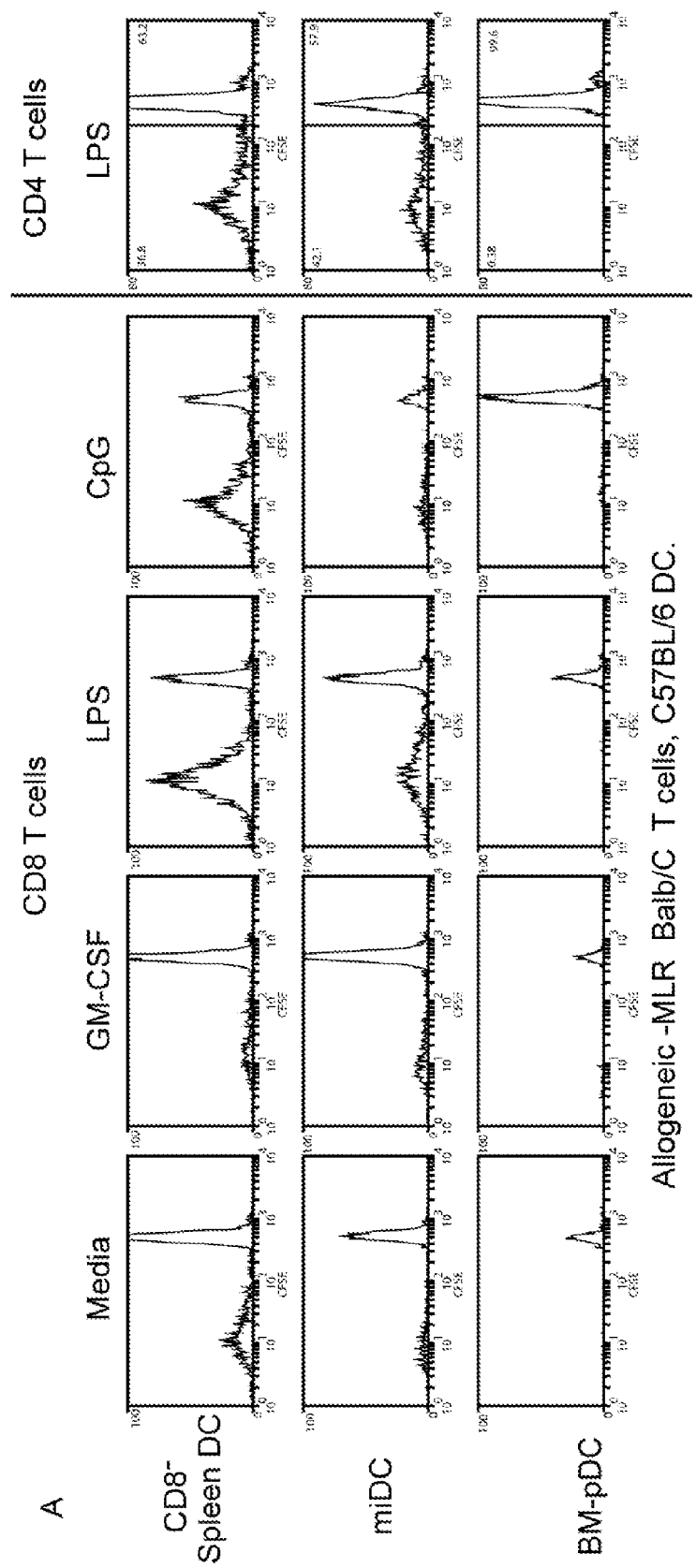
FIG. 8A-C depict that miDC are potent stimulators of antigen-specific T cells. A. Allogeneic MLR: miDC, BM pDC or spleen cDC from C57BL/6 mice were purified and incubated with Balb/c lymph node T cells labelled with CFSE. Stimulants were added to the cultures as shown. CFSE expression by the T cells was analysed 3 days later. FACS data is representative of pooled triplicate wells. Data are representative of two separate experiments. B. miDC, BMpDC or spleen CD8+ or CD8− cDC were incubated with MVA-OVA for 1 h at 37° C., then washed. Titrated DCs were then added to 50,000 CFSE-labelled OTI T cells. Data shown is for $10^4$ DC of each subtype. CFSE fluorescence of OTI T cells was measured by FACS three days later and number of proliferating cells quantitated by reference to a known number of quantibeads spiked into each well before harvesting the cells. Shown are values of pooled triplicate wells. Data is representative of three separate experiments. C. miDC were incubated with soluble ovalbumin and incubated at 37° C. for 1 h, then washed. $10^4$ DC with added stimulus as shown were added to 50,000 OTI T cells and CFSE proliferation was analysed 3 days later. Data are results from pooled triplicate wells of one experiment and are representative of two experiments.
Figure 8B:
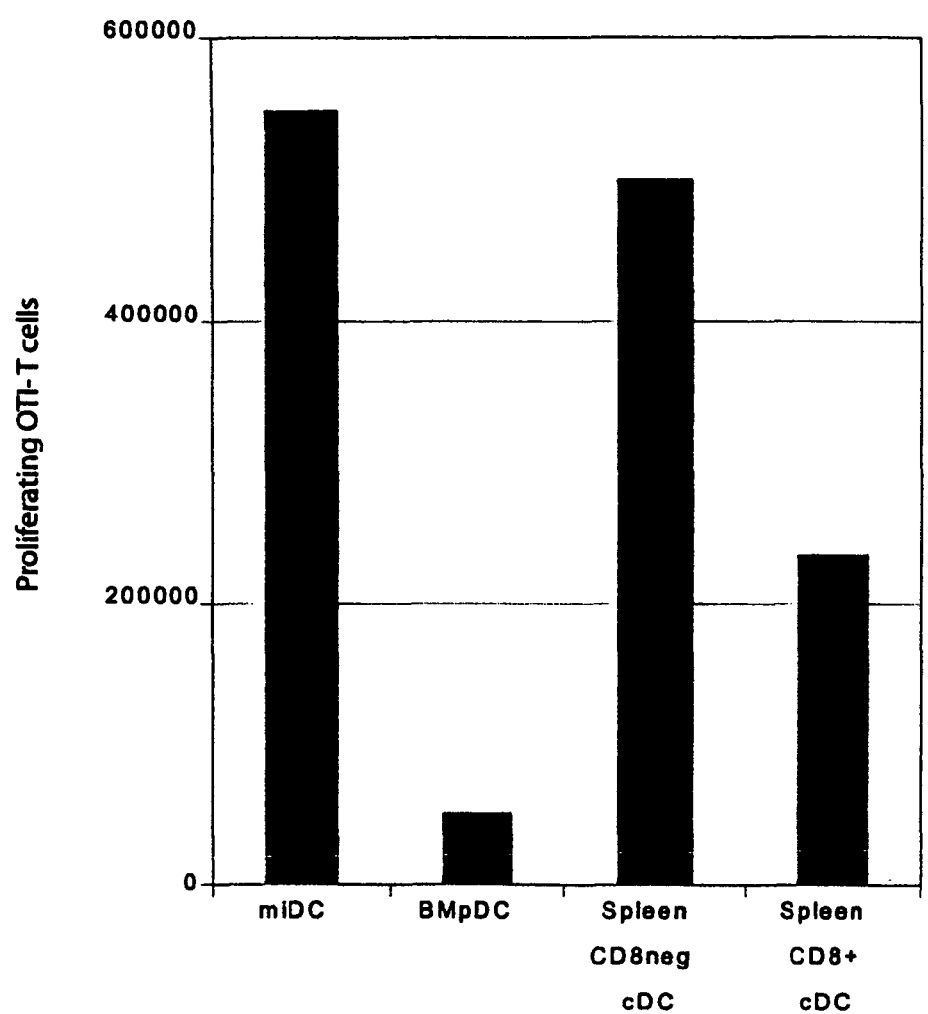

With activation, the miDC stimulated naive T cells (FIG. 8A), more efficiently than pDC albeit to a lesser extent than CD8⁻ spleen DC.

To determine whether the miDC had the capacity to stimulate antigen-specific T cells, they were co-incubated with MVA expressing Ovalbumin (MVA-OVA) under an early viral promoter. The cells were washed after 1 h and then co-incubated with OTI-T cells. The MVA-OVA stimulated miDC clearly presented the virally encoded antigen and were far more effective at stimulating the OTI T cells than the pDC. In fact, they were at least as efficient as CD8⁻ spleen cDC and more efficient than CD8⁺ spleen cDC in stimulating the OTI cells.

Figure 8C:
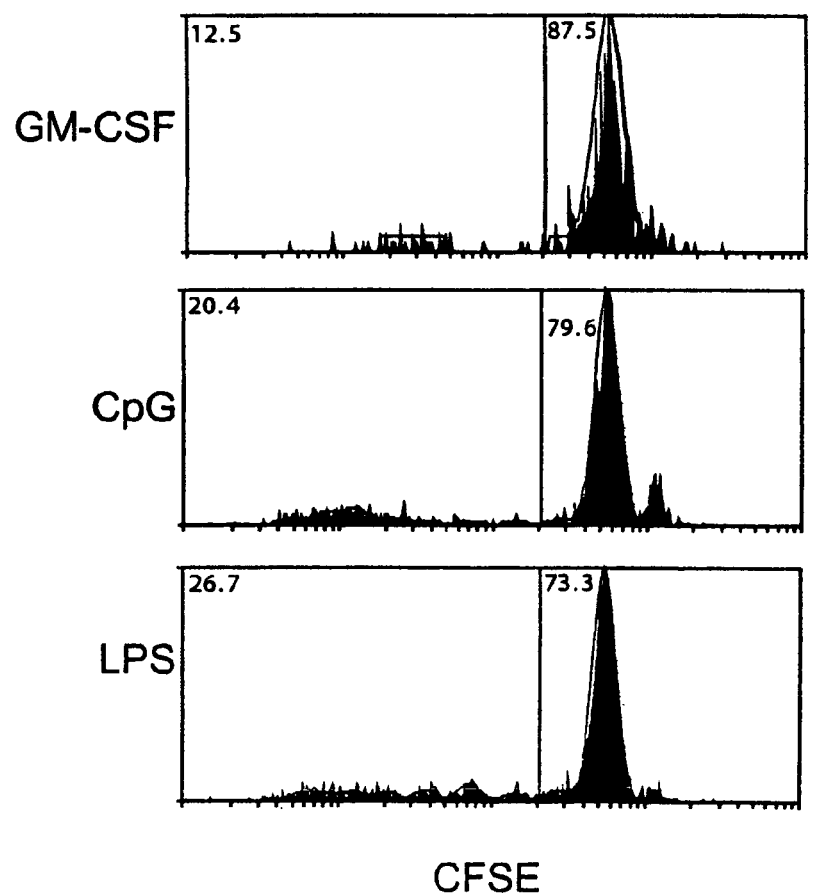

The capacity of the miDC to cross-present antigen was also tested. Like pDC and CD8-cDC, the miDC were inefficient at cross-presenting peptides from soluble ovalbumin (FIG. 8C).

Thus, a BM cell that produces high levels of IFN-α in response to TLR9 ligands and certain viruses and that is highly efficiently at stimulating naive T cells, particularly when presenting viral-encoded antigen, has been identified. With TLR reactivity (TLR2, 4, 7 and 9), presentation capacity, and phenotype in FLDC cultures, they resemble the mouse CD8⁻ cDC. However, together with their upregulation of CD8α and IFN α production to TLR7 and 9 ligands and viral responses they stand apart as a unique cell type.

REFERENCES

Diebold 2009. Activation of dendritic cells by toll-like receptors and C-type lectins. Handb. Exp. Pharmacol. 188:3-30.

Hochrein and O'Keeffe 2008. Dendritic cell subsets and toll-like receptors. Handb. Exp. Pharmacol. 183:153-179.

Luber et al. 2010. Quantitative proteomics reveals subset-specific viral recognition in dendritic cells. Immunity 32(2):279-289.

O'Keeffe et al. 2003. Dendritic cell precursor populations of mouse blood: identification of the murine homologues of human blood plasmacytoid pre-DC2 and CD11c+ DC1 precursors. Blood 101(4):1453-1459.

Villadangos and Schnorrer 2007. Intrinsic and cooperative antigen-presenting functions of dendritic-cell subsets in vivo. Nat. Rev. Immunol. 7(7):543-555.

Hochrein et al. 2001. Differential production of IL-12, IFN-alpha, and IFN-gamma by mouse dendritic cell subsets. J. Immunol. 166(9):5448-5455.

Maldonado-Lopez et al. 1999. CD8alpha+ and CD8alpha– subclasses of dendritic cells direct the development of distinct T helper cells in vivo. J. Exp. Med. 189(3):587-592.

Proietto et al. 2004. Differential production of inflammatory chemokines by murine dendritic cell subsets. Immunobiology 209(1-2):163-172.

O'Keeffe et al. 2002a. Mouse plasmacytoid cells: long-lived cells, heterogeneous in surface phenotype and function, that differentiate into CD8(+) dendritic cells only after microbial stimulus. J. Exp. Med. 196(10):1307-1319.

Villadangos and Young 2008. Antigen-presentation properties of plasmacytoid dendritic cells. Immunity 29(3):352-361.

Young et al. 2008. Differential MHC class II synthesis and ubiquitination confers distinct antigen-presenting properties on conventional and plasmacytoid dendritic cells Nat. Immunol. 9(11):1244-1252.

Gilliet et al. 2008. Plasmacytoid dendritic cells: sensing nucleic acids in viral infection and autoimmune diseases. Nat. Rev. Immunol. 8(8):594-606.

Kadowaki 2009. The divergence and interplay between pDC and mDC in humans. Front. Biosci. 14:808-817.

Hochrein et al. 2004. Herpes simplex virus type-1 induces IFN-alpha production via Toll-like receptor 9-dependent and -independent pathways. Proc. Natl. Acad. Sci. USA 101(31):11416-11421.

Chen et al. 2004. Thrombopoietin cooperates with FLT3-ligand in the generation of plasmacytoid dendritic cell precursors from human hematopoietic progenitors., Blood 103(7):2547-2553.

Kawano et al. 1995. Differentiation of early plasma cells on bone marrow stromal cells requires interleukin-6 for escaping from apoptosis. Blood 85(2):487-494.

McKenna et al. 2000. Mice lacking flt3 ligand have deficient hematopoiesis affecting hematopoietic progenitor cells, dendritic cells, and natural killer cells. Blood 95(11):3489-3497.

Ogilvy et al. 1999. Constitutive Bcl-2 expression throughout the hematopoietic compartment affects multiple lineages and enhances progenitor cell survival 2. Proc. Natl. Acad. Sci. USA 96(26):14943-14948.

O'Keeffe et al. 2002b. Effects of administration of progenipoietin 1, Flt-3 ligand, granulocyte colony-stimulating factor, and pegylated granulocyte-macrophage colony-stimulating factor on dendritic cell subsets in mice. Blood 99(6):2122-2130.

Spies et al. 2003. Vaccination with plasmid DNA activates dendritic cells via Toll-like receptor 9 (TLR9) but functions in TLR9-deficient mice. J. Immunol. 171(11):5908-5912.

Blom et al. 2000. Generation of interferon alpha-producing predendritic cell (Pre-DC)2 from human CD34(+) hematopoietic stem cells. J. Exp. Med. 192(12):1785-1796.

Liu et al. 2007. Origin of dendritic cells in peripheral lymphoid organs of mice. Nat. Immunol. 8(6):578-583.

Naik et al. 2006. Intrasplenic steady-state dendritic cell precursors that are distinct from monocytes. Nat. Immunol. 7(6):663-671.

Naik et al. 2007. Development of plasmacytoid and conventional dendritic cell subtypes from single precursor cells derived in vitro and in vivo. Nat. Immunol. 8(11):1217-1226.

O'Keeffe et al. 2005. Distinct roles for the NF-kappaB1 and c-Rel transcription factors in the differentiation and survival of plasmacytoid and conventional dendritic cells activated by TLR-9 signals. Blood 106(10):3457-3464.

Pelayo et al. 2005. Derivation of 2 categories of plasmacytoid dendritic cells in murine bone marrow. Blood 105(11):4407-4415.

The invention claimed is:

1. An in vitro method for detecting the presence or absence of $CD11b^{-/lo}$, $CD172^+$ (Sirpα), $CD45RA^-$, $CD24^{int}$ dendritic cells producing interferon-alpha ("IFN-α"), comprising the steps of:
   (a) separating bone marrow cells from plasmacytoid dendritic cells and conventional dendritic cells by removing $CD45RA^+$ cells and $CD11b^{hi}$ cells to prepare bone marrow cells comprising $CD11b^{-/lo}$, $CD172^+$ (Sirpα), $CD45RA^-$, $CD24^{int}$ dendritic cells;
   (b) incubating the separated bone marrow cells with at least one of a toll-like receptor-3 ("TLR3") ligand, a toll-like receptor-7 ("TLR7") ligand, and a toll-like receptor-9 ("TLR9") ligand;
   (c) detecting whether IFN-α is produced; and
   (d) if IFN-α is produced, isolating or enriching $CD11b^{-/lo}$, $CD172^+$ (Sirpα), $CD45RA^-$, $CD24^{int}$ dendritic cells producing IFN-α.

2. The method of claim 1, wherein the bone marrow cells are separated from pDCs using an anti-CD45RA antibody.

3. The method of claim 1, wherein the IFN-α-producing dendritic cells are characterized by the following surface markers: CD11c+, BDCA-1+, CD172+(Sirpα), CD11b$^{-/lo}$, CD45RA−, CD3−, CD19−, CD20−, CD49b−, NK1.1−, Ly6G−, and CD8α−.

4. The method of claim 1, comprising incubating the cell population with a toll-like receptor-3 ("TLR3") ligand.

5. The method of claim 1, comprising incubating the cell population with a toll-like Withdrawn-7 ("TLR7") ligand.

6. The method of claim 5, wherein the TLR7 ligand is R837.

7. The method of claim 1, comprising incubating the cell population with a toll-like receptor-9 ("TLR9") ligand.

8. The method of claim 7, wherein the TLR9 ligand is CpG-2216-ODN.

9. The method of claim 1, further comprising loading the CD11b$^{-/lo}$, CD172$^+$ (Sirpα), CD45RA$^-$, CD24$^{int}$ dendritic cells producing IFN-α ex vivo with one or more antigens.

10. An in vitro method for detecting the presence or absence of interferon-alpha ("IFN-α") production comprising:
   (a) separating bone marrow cells from plasmacytoid dendritic cells and conventional dendritic cells by removing CD45RA$^+$ cells and CD11b$^{hi}$ cells;
   (b) isolating CD11b$^{-/lo}$, CD172$^+$ (Sirpα), CD45RA$^-$, CD24$^{int}$ dendritic cells;
   (c) incubating the CD11b$^{-/lo}$, CD172$^+$ (Sirpα), CD45RA$^-$, CD24$^{int}$ dendritic cells with at least one of a toll-like receptor-3 ("TLR3") ligand, a toll-like receptor-7 ("TLR7") ligand, and a toll-like receptor-9 ("TLR9") ligand; and
   (d) detecting whether IFN-α is produced from the CD11b$^{-/lo}$, CD172$^+$ (Sirpα), CD45RA$^-$, CD24$^{int}$ dendritic cells.

11. The method of claim 10, wherein the bone marrow cells are separated from pDCs using an anti-CD45RA antibody.

12. The method of claim 10, wherein the IFN-α-producing dendritic cells are characterized by the following surface markers: CD11c+, BDCA-1+, CD172+(Sirpα), CD11b$^{-/lo}$, CD45RA−, CD3−, CD19−, CD20−, CD49b−, NK1.1−, Ly6G−, and CD8α−.

13. The method of claim 10, comprising incubating the cell population with a toll-like receptor-3 ("TLR3") ligand.

14. The method of claim 10, comprising incubating the cell population with a toll-like receptor-7 ("TLR7") ligand.

15. The method of claim 14, wherein the TLR7 ligand is R837.

16. The method of claim 10, comprising incubating the cell population with a toll-like receptor-9 ("TLR9") ligand.

17. The method of claim 16, wherein the TLR9 ligand is CpG-2216-ODN.

18. The method of claim 10, further comprising loading the CD11b$^{-/lo}$, CD172$^+$ (Sirpα), CD45RA$^-$, CD24$^{int}$ dendritic cells producing IFN-α ex vivo with one or more antigens.

* * * * *